(12) United States Patent
Riesinger

(10) Patent No.: US 11,154,426 B2
(45) Date of Patent: Oct. 26, 2021

(54) WOUND CARE DEVICE FOR THE TREATMENT OF WOUNDS BY MEANS OF ATMOSPHERIC NEGATIVE PRESSURE, COMPRISING A WINDOW THAT CAN BE OPENED

(71) Applicant: BSN MEDICAL GMBH, Hamburg (DE)

(72) Inventor: Birgit Riesinger, Munster (DE)

(73) Assignee: BSN medical GmbH, Hamburg (DE)

( * ) Notice: Subject to any disclaimer, the term of this patent is extended or adjusted under 35 U.S.C. 154(b) by 52 days.

(21) Appl. No.: 14/942,038

(22) Filed: Nov. 16, 2015

(65) Prior Publication Data

US 2016/0135998 A1 May 19, 2016

Related U.S. Application Data

(63) Continuation of application No. PCT/EP2014/060133, filed on May 16, 2014.

(30) Foreign Application Priority Data

May 16, 2013 (DE) ...................... 10 2013 105 063.8
Jul. 12, 2013 (DE) ...................... 10 2013 107 399.9

(51) Int. Cl.
*A61M 1/00* (2006.01)
*A61F 13/00* (2006.01)
(Continued)

(52) U.S. Cl.
CPC .................. *A61F 13/00068* (2013.01); *A61F 2013/0057* (2013.01); *A61F 2013/00182* (2013.01);
(Continued)

(58) Field of Classification Search
CPC ........ A61M 1/00; A61M 13/02; A61M 27/00; A61F 13/00; A61F 13/02;
(Continued)

(56) References Cited

U.S. PATENT DOCUMENTS 4,468,227 A 8/1984 Jensen
5,086,763 A * 2/1992 Hathman ............ A61F 13/0246
128/887

(Continued)

FOREIGN PATENT DOCUMENTS

DE 2086484 * 9/2007
EP 1 814 609 8/2007 .............. A61M 1/00
(Continued)

OTHER PUBLICATIONS

International Preliminary Report on Patentability issued in corresponding foreign application, PCT/EP2014/184366, pp. 1-6 (dated Nov. 17, 2015).

(Continued)

*Primary Examiner* — Tatyana Zalukaeva
*Assistant Examiner* — Ilya Y Treyger
(74) *Attorney, Agent, or Firm* — Rankin, Hill & Clark LLP

(57) ABSTRACT

A wound care device for the treatment of wounds is disclosed by means of atmospheric negative pressure in the wound region, including a wound-covering element that can be attached to the skin of a patient as well as a connection device for the suctioning of fluid media, wherein the wound-covering element includes a window that can be opened, which window is arranged on the wound-covering element by means of a gas-tight closure.

21 Claims, 20 Drawing Sheets

(51) Int. Cl.
    *A61M 27/00*     (2006.01)
    *A61F 13/02*     (2006.01)
    *A61B 17/50*     (2006.01)

(52) U.S. Cl.
    CPC ........... *A61F 2013/00574* (2013.01); *A61F 2013/00731* (2013.01); *A61F 2013/00936* (2013.01); *A61M 1/90* (2021.05)

(58) Field of Classification Search
    CPC .... A61F 2013/00182; A61F 2013/0057; A61F 2013/00574; A61F 2013/00731; A61F 2013/00936; A61B 17/50
    See application file for complete search history.

(56) References Cited

U.S. PATENT DOCUMENTS

| | | | | |
|---|---|---|---|---|
| 5,759,560 | A * | 6/1998 | Dillon | A61L 15/125 |
| | | | | 424/402 |
| 7,534,240 | B1 * | 5/2009 | Johnson | A61F 13/00063 |
| | | | | 602/43 |
| 7,922,703 | B2 * | 4/2011 | Riesinger | A61F 13/00068 |
| | | | | 604/305 |
| 8,298,200 | B2 * | 10/2012 | Vess | A61M 1/0023 |
| | | | | 604/313 |
| 2004/0193130 | A1 * | 9/2004 | Fima | A61F 13/495 |
| | | | | 604/385.01 |
| 2007/0265586 | A1 | 11/2007 | Joshi et al. | |
| 2008/0119802 | A1 | 5/2008 | Riesinger | |

FOREIGN PATENT DOCUMENTS

| | | | | |
|---|---|---|---|---|
| JP | 2011035038 A * | 5/2000 | | |
| JP | 2008073163 A | 4/2008 | | |
| JP | 2009533085 A | 9/2009 | | |
| JP | 201331786 A | 2/2013 | | |
| WO | 2007117655 A2 | 10/2007 | | |
| WO | WO 2012/168298 | 12/2012 | ............. | A61M 1/00 |

OTHER PUBLICATIONS

International Search Report issued in corresponding foreign application, PCT/EP2014/184366, pp. 1-2 (dated Nov. 20, 2014).
Written Opinion issued in corresponding foreign application, PCT/EP2014/184366, pp. 1-5 (dated Nov. 16, 2015).
Office Action dated Feb. 27, 2018 for the corresponding Japanese Patent Application No. 2016-513395; English translation.

* cited by examiner

WOUND CARE DEVICE FOR THE TREATMENT OF WOUNDS BY MEANS OF ATMOSPHERIC NEGATIVE PRESSURE, COMPRISING A WINDOW THAT CAN BE OPENED

CROSS-REFERENCE TO RELATED APPLICATIONS

The present application claims priority from and is a continuation of PCT Application Serial No. PCT/EP2014/060133, filed May 16, 2014; which claims priority from German Patent Application No. DE 10 2013 105 063.8, filed May 16, 2013 and German Patent Application Serial No. DE 10 2013 107 399.9, filed Jul. 12, 2013, all of which are herein incorporated by reference in their entireties.

BACKGROUND

The invention relates to a wound care device for the treatment of wounds by means of atmospheric negative pressure, comprising a window that can be opened.

Conventional systems and devices for the treatment of wounds by means of atmospheric negative pressure consist of a gas-tight wound covering, a drainage hose, a externally positioned vacuum pump, as well as a vessel for the collection of discharged exudates Such devices have been described, for example, in U.S. Pat. No. 7,198,046. In EP1814609, a wound care device for the treatment of wounds by means of atmospheric negative pressure is described. This wound care device may optionally feature a window that can be opened, which is referred to as a "gas-tight treatment window", or also as a "tiltable closing element"

Devices for the treatment of wounds by means of atmospheric negative pressure are used, for example, for postoperative treatment of incisions (when the objective is to drain the exudate, and thus to allow for a faster healing of sutures with fewer complications), as well as for the treatment of deep-set edemas, for example in case of pressure sores or venous ulcers (where the active acquisition of wound fluid from deep inside is a precondition for the healing of a chronical wound).

Typically, in this form of therapy, relative negative pressures of between 60 and 200 mm Hg are used. The window that can be opened described in EP1814609 allows for a wound contact element positioned underneath it, for example an absorption element or a secondary care product, to be inserted into the space formed by the gas-tight wound covering, or to be removed from that space. In this way, said wound contact element or said care product can be removed from the wound space, for example for the purpose of wound cleansing or for replacing it, without it being necessary to replace the entire wound care device, which is preferably attached to patient's skin around the wound. This, in turn, reduces traumatic interventions in the wound treatment process, and has cost-related advantages as well.

Based on the atmospheric conditions, it is necessary that said window that can be opened is gas-tight when it is in a closed position. This is not trivial, because air is a very low-viscosity medium. Moreover, many types of gas-tight bonds also require a strong physical bond, which is undesirable in terms of contact with the wound, since such strong physical bonds are characterized by a certain height and a certain weight on the one hand, and by a certain resilience when opening or closing—in other words: opening and closing are done by means of manual strength—on the other hand.

In the present context, however, this is highly undesirable, since the exertion of force in the wound region can often lead to exposure of the patient to pain. If, for example, the closing of a treatment window would require the use of force, the patient would experience this as a traumatic intervention, especially in cases of scars, pressure sores and venous ulcers.

The task of the present invention is therefore to provide a vacuum wound treatment that would allow for the exchange of wound contact elements or care products without the aforementioned disadvantages.

SUMMARY OF THE INVENTION

Provided herein are systems, methods and compositions for a wound care device for the treatment of wounds by means of atmospheric negative pressure in the wound region, comprising a wound-covering element that can be attached to the skin of a patient as well as a connection device for the suctioning of fluid media, characterized in that the wound-covering element comprises a window that can be opened, which window is arranged on the wound-covering element by means of a gas-tight closure.

The methods, systems, and apparatuses are set forth in part in the description which follows, and in part will be obvious from the description, or can be learned by practice of the methods, apparatuses, and systems. The advantages of the methods, apparatuses, and systems will be realized and attained by means of the elements and combinations particularly pointed out in the appended claims. It is to be understood that both the foregoing general description and the following detailed description are exemplary and explanatory only and are not restrictive of the methods, apparatuses, and systems, as claimed.

BRIEF DESCRIPTION OF THE DRAWINGS

In the accompanying figures, like elements are identified by like reference numerals among the several preferred embodiments of the present invention.

DETAILED DESCRIPTION OF THE INVENTION

Figure 1:
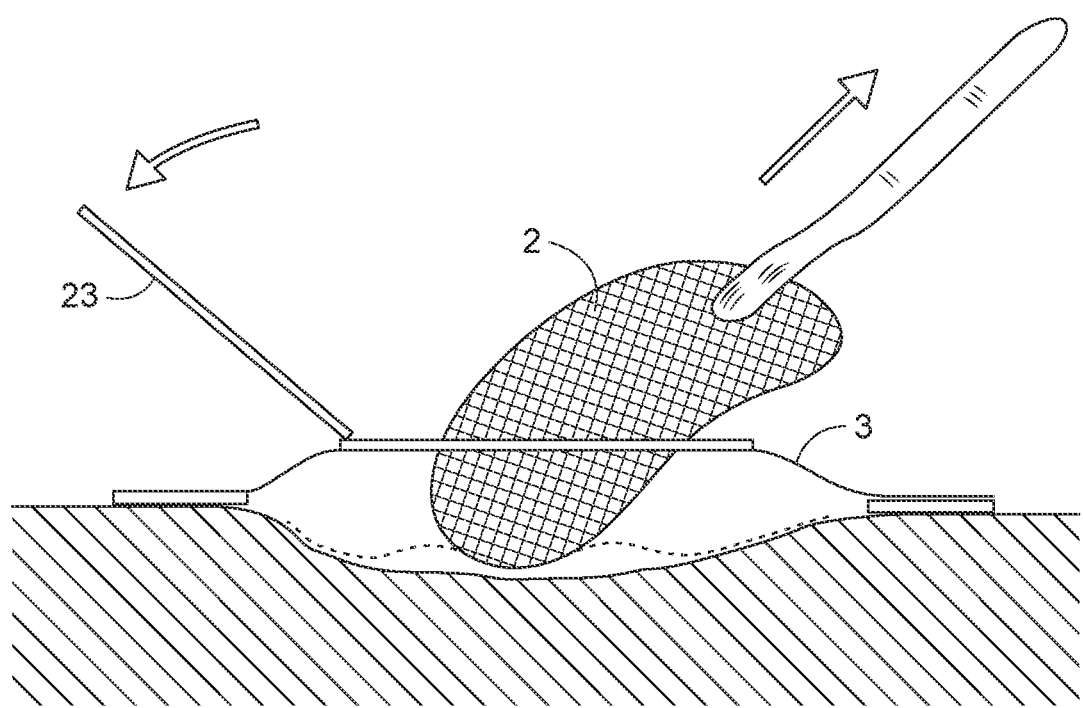
FIG. 1 is a side view of the wound care device for the treatment of wounds by means of atmospheric negative pressure in the wound region, comprising a wound-covering element 3 that can be attached to the skin of a patient, as well as a connection device (not shown) for the suctioning of fluid media, according to one embodiment.

The foregoing and other features and advantages of the invention are apparent from the following detailed description of exemplary embodiments, read in conjunction with the accompanying drawings. The detailed description and drawings are merely illustrative of the invention rather than limiting, the scope of the invention being defined by the appended claims and equivalents thereof.

Embodiments of the invention will now be described with reference to the Figures, wherein like numerals reflect like elements throughout. The terminology used in the description presented herein is not intended to be interpreted in any limited or restrictive way, simply because it is being utilized in conjunction with detailed description of certain specific embodiments of the invention. Furthermore, embodiments of the invention may include several novel features, no single one of which is solely responsible for its desirable attributes or which is essential to practicing the invention described herein. The words proximal and distal are applied herein to denote specific ends of components of the instrument described herein. A proximal end refers to the end of an instrument nearer to an operator of the instrument when the instrument is being used. A distal end refers to the end of a component further from the operator and extending towards the surgical area of a patient and/or the implant.

The use of the terms "a" and "an" and "the" and similar referents in the context of describing the invention are to be construed to cover both the singular and the plural, unless otherwise indicated herein or clearly contradicted by context.

Recitation of ranges of values herein are merely intended to serve as a shorthand method of referring individually to each separate value falling within the range, unless otherwise indicated herein, and each separate value is incorporated into the specification as if it were individually recited herein. The word "about," when accompanying a numerical value, is to be construed as indicating a deviation of up to and inclusive of 10% from the stated numerical value. The use of any and all examples, or exemplary language ("e.g." or "such as") provided herein, is intended merely to better illuminate the invention and does not pose a limitation on the scope of the invention unless otherwise claimed. No language in the specification should be construed as indicating any non-claimed element as essential to the practice of the invention.

References to "one embodiment," "an embodiment," "example embodiment," "various embodiments," etc., may indicate that the embodiment(s) of the invention so described may include a particular feature, structure, or characteristic, but not every embodiment necessarily includes the particular feature, structure, or characteristic. Further, repeated use of the phrase "in one embodiment," or "in an exemplary embodiment," do not necessarily refer to the same embodiment, although they may.

The invention provides a wound care device for the treatment of wounds by means of atmospheric negative pressure in the wound region, comprising a wound-covering element that can be attached to the skin of a patient, as well as a connection device for the suctioning of fluid media, the wound-covering element having a window that can be opened, which window is arranged by means of a gas-tight closure on the wound-covering element.

Said window that can be opened features a number of advantages. So, for instance, it allows for an easier rinsing or cleansing of the underlying wound, the treatment of that wound with pharmaceutics or care products, a non-traumatic replacement of a wound dressing or of an absorption element the inspection and evaluation of the wound, and the taking of samples, for instance a swab, without a need for removing the entire wound care device.

The "window that can be opened" concept includes completely transparent windows, as well as windows that are not transparent or which have a non-transparent material underneath them, as well as windows that feature a transparent section.

Preferentially, the wound-covering element is pre-formed so as to correspond to the anatomic relief of a certain body position. This may be useful, for example, when the wound-covering element is to be applied to the elbow, hip, or knee areas. A deep-drawing process, for example, allows for the pre-forming of the wound-covering element so as to correspond to the anatomic relief of the aforementioned body positions.

Also preferentially, the wound-covering element is embodied such that it can adjust to the movements of a given body position. For these purposes, for example, the wound-covering element and the gas-tight closure may be embodied in an elastic manner. Furthermore, a pleated arrangement or one or several stretch bellows may be provided.

In the aforementioned embodiments it is particularly important that the aforementioned gas-tight closure will retain its gas-tightness property even under these aggravated conditions.

Preferentially, the aforementioned gas-tight closure is embodied in the form of a interlocking seal. In what follows, the concept of "interlocking seal" will refer to all types of disclosed interlocking seals that function according to the tongue-and-groove principle.

For these purposes, both parts that are to be connected with each other by means of the seal feature lips that interlock with each other when the seal is applied. Preferentially, these lips consist of elastic materials, such as synthetic or natural rubber, polyethylene, or polypropylene.

Such seals are known, for example from resealable carry-on pouches for the transportation of cosmetics during air travel, resealable storage bags for frozen food storage, or resealable storage boxes ("Tupperware").

The aforementioned interlocking seals are also known under the pseudonyms of "Ziplock", "Minigrip", or sliding closure. In the latter case, a slider can be provided which slides along to lips that are to be sealed similar to a zipper, and moves them into the sealed position.

So-called bulge locks, as described, for example in WO03013976A1, are included within the concept of "interlocking seals".

It is important that the aforementioned seals are suited for a gas-tight closure of said window that can be opened when it is in a closed position, and furthermore, that they have or require a low height and a low weight, and also, that they require only a small degree of force for closing or opening them. In this way, the opening or closing can be done without exposure [of the patient] to pain.

Figure 4A:
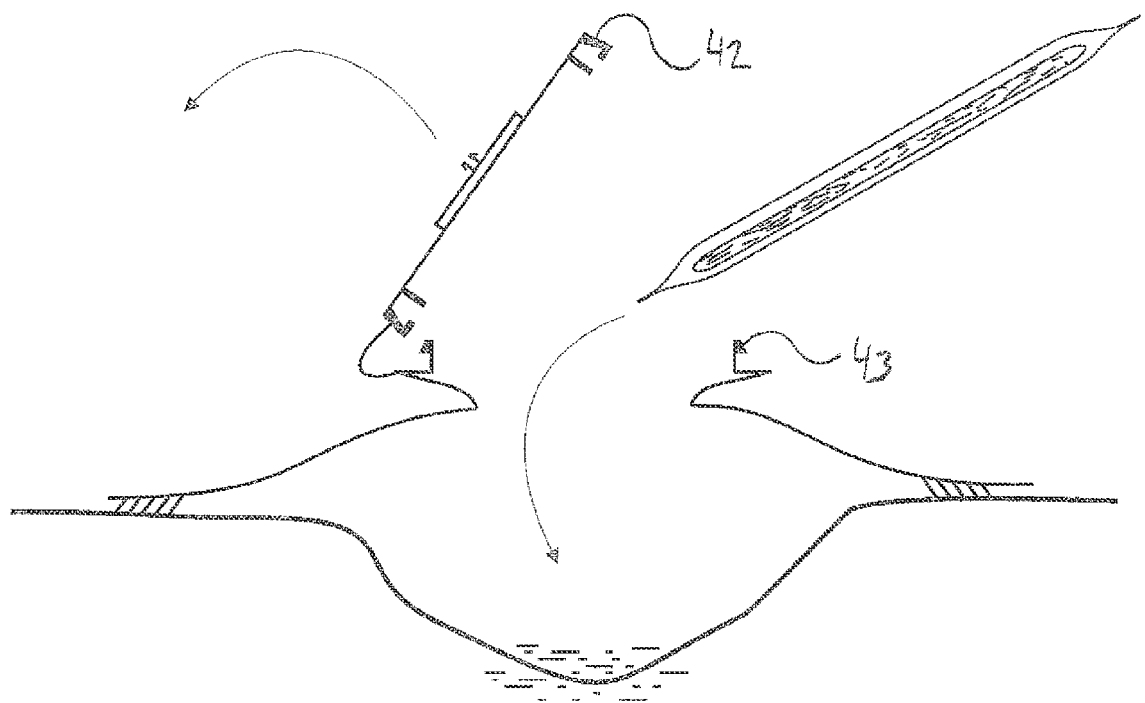
FIG. 4a is a side view of a window that can be opened with an interlocking seal 42, 43, according to one embodiment.
Figure 4B:
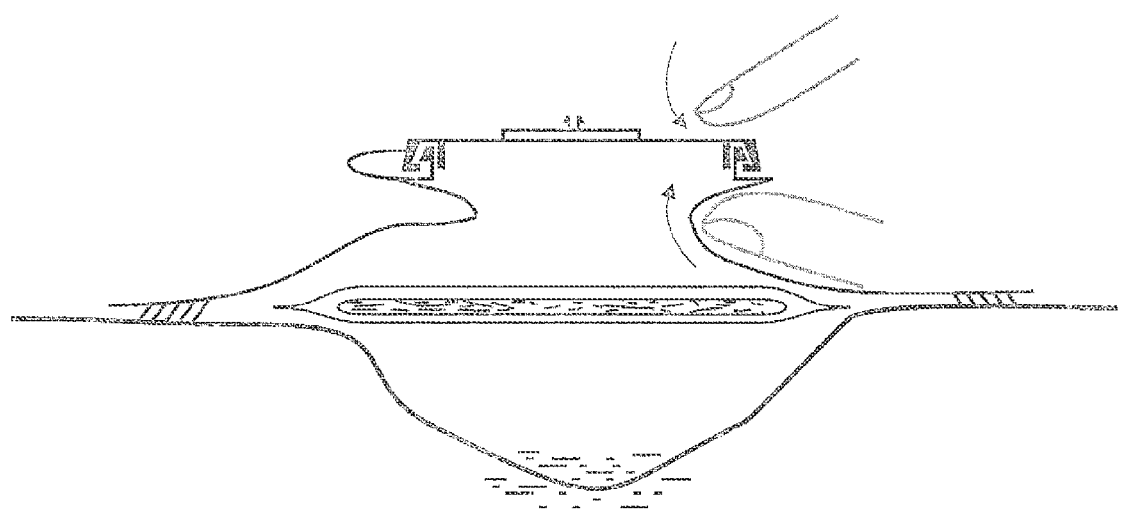
FIG. 4b is a side view of the interlocking seal features in the closed position, according to one embodiment.

The latter can be achieved, for example by means of an embodiment with a slider (see FIG. 9 and description) or an embodiment with a tongue and groove option (see FIG. 4 and description).

As an alternative to the aforementioned embodiment, said gas-tight closure may be embodied in the form of a magnetic seal. For these purposes, flexible ferromagnetic strips may be specifically provided. The aforementioned magnetic seal features similar advantages with respect to operability. It may be embodied in a gas-tight as well. It may also be technically embodied in such a manner that it retains its gas-tightness even under the aforementioned aggravated conditions.

As an alternative to the aforementioned embodiment, said gas-tight closure may be embodied in the form of an adhesive seal. For these purposes, two foils are attached to each other in a sealing zone. By means of an opening strap, the first foil can easily be detached from second foil, which exposes the adhesive layer integrated in a recess. The lower sheet consists of a polyester support layer, an adhesive layer that is sensitive to pressure, and a sealing layer with an integrated migration barrier. The strengths are between 200 and 500 μm. The aforementioned adhesive seal is known, for example, from EP2067717, and features similar advantages with respect to operability. It may be embodied in a gas-tight form as well. It may also be technically embodied in such a manner that it retains its gas-tightness even under the aforementioned aggravated conditions.

As an alternative to the aforementioned embodiment, said gas-tight closure may be embodied in the form of a tongue and groove seal, possibly featuring an internal sealing lip. The aforementioned tongue and groove seal features similar advantages with respect to operability. It may be embodied in a gas-tight form as well. It may also be technically embodied in such a manner that it retains its gas-tightness even under the aforementioned aggravated conditions.

As an alternative to the aforementioned embodiment, said gas-tight closure may be embodied in the form of a rubber seal or of a rubber tube, possibly with a means of pressurization. As an alternative to the aforementioned embodiment, said gas-tight closure may be embodied in the form of a cork strip, possibly with a means of pressurization.

This means of pressurization may be embodied, for example as a bracket or as the aforementioned tongue and groove seal.

As an alternative to the aforementioned embodiment, said gas-tight closure may be embodied in the form of an adhesive seal, for example by means of a low-adhesive silicone adhesive applied to the frame side or the window side, preferably in the form of a film or a coating. An acrylic adhesive may be used as well. Apart from favorable sealing and adhesive properties, they have the advantage that they are physiologically safe.

Preferentially, the wound-covering element can be attached to the skin of a patient by means of an adhesive material. For these purposes, every type of physiologically acceptable adhesive can be used, in particular medical-grade adhesives. Particularly preferred are materials selected from the group containing acrylic adhesives, silicone, hydrocolloid adhesives, zinc-oxide adhesives, and/or latex adhesives.

Hydrocolloid adhesives generally consist of a thin polymer film that is applied to a self-adhesive substance. The carrier substance (such as synthetic rubber types, for example poly-isobutylene) contains swelling particles, which vary, depending on the manufacturer. Often, swelling particles such as carboxymethyl cellulose or sodium carboxymethyl cellulose are included. Furthermore, they are very malleable, especially when warm. Hydrocolloid adhesives are suitable for being worked into surfaces, and are specifically capable of removing moisture. They are available in paste form, but also panel or strip form.

Something similar applies to silicone materials. The degree of adhesiveness to the skin can be regulated with these materials, so that despite the adhesiveness, a non-traumatic replacement of wound dressings can be ensured.

Preferentially, such silicone adhesives can be embodied in the form of a detachable self-adhesive laminate, which comprises a structural layer, with a wound-facing side to which a hydrophobic gel is applied, for example in the form of a silicone gels, and a side facing away from the wound, which carries an adhesive for example in the form of an acrylic adhesive. One such layer was described, for example in EP2001424B1.

Preferentially, said adhesive material is embodied in the form of a "border dressing" as a adhesive edge, which peripherally surrounds the wound-covering element.

Said adhesive material may also be embodied in the form of a panel or a strip on which the wound-covering element is distally positioned. In this embodiment, said panel or strip may feature a central opening, which is intended to be positioned over the wound. In that embodiment, said panel or strip takes the shape of a frame. Alternatively, said panel or strip may be embodied such that a window may be cut into the panel or the strip, corresponding in shape to the outline of the wound. For these purposes, the outline of the wound may be drawn on it, and then cut out with a pair of scissors. Alternatively, a template may be used, by means of which the outline of the wound can be transferred to the panel or the strip, or by means of which [an opening corresponding to] the outline of the wound can be cut out of the panel or the strip.

Said panel or said frame consists, for example of a hydrocolloid material as described herein. Said strip consists, for example, of a so-called incision foil, which is a self-adhesive foil made out of a polymer material.

Alternatively, said panel or said frame consists of a foam material and/or a spacer fabric. Preferentially, it is worked into a gas-tight cover. On the skin-facing side, the aforementioned adhesives may be applied.

Further preferentially, the device features a wound exudate-extracting absorption element.

This makes it possible to ensure that it is not necessary to channel all the wound exudate generated by the negative pressure therapy into an external canister, and that at least part of it can remain in the wound space. It may then be removed through a simple replacement of the absorption element, and since it is bound to the absorption element, it can be disposed of in an easier and more hygienic manner than an exudate canister.

The resulting possibility of dispensing with an external canister has additional advantages. For example, the device may be embodied such that the patient's mobility is retained (meaning that he is able to leave his bed and pursue his regular daily routines)

Further preferentially, the absorption element features at least one super-absorbing substance, a modified cellulose, a foam material, and/or an alginate.

Preferentially in particular, the absorption element also features a fleece comprising cellulose fibers.

Super-absorbing polymers (SAPs) are synthetic materials capable of absorbing multiple times their own weight of fluids—up to 1000 times their own weight. In chemical terms, these are copolymers of acrylic acid (propenoic acid, $C_3H_4O_2$) and sodium acrylate (sodium salt from acrylic acid, $NaC_3H_3O_2$), in which the mutual relationship between the two monomers may vary. Furthermore, a so-called core cross-linker (CXL) is added to the monomer solution, which interlinks the formed long-chain polymer molecules in places by means of chemical bridges. As a result of these bridges, the polymer becomes insoluble in water. When water or aqueous saline solutions penetrate the polymer particle, it swells up, and stretches this network of bonds on a molecular level, so that water can no longer escape unassisted. The super-absorbing polymers can be used in the wound care device according to the invention in the form of a granulate, a powder, a fill, pellets, a foam, in the form of fibers, or a fibrous fabric, mat, fleece, and/or fibrous wads.

Preferentially, modified cellulose are derivatives of cellulose, preferentially sulphoalkyl cellulose and its derivatives, preferentially cellulose ethyl sulfonates, carboxyalkyl cellulose, preferentially carboxymethyl cellulose, carboxyethyl cellulose, and/or carboxypropyl cellulose, more complex cellulose derivatives such as sulphoethyl carboxymethyl cellulose, carboxymethyl hydroxylethyl cellulose, hydroxypropyl methyl cellulose, and amidated cellulose derivatives such as carboxymethyl cellulose amid or carboxypropyl cellulose amid. Carboxymethyl cellulose is particularly available in the form of sodium carboxymethyl cellulose, and commercial available as "hydro fiber". In hygienic and wound care products, the fibers are used in a flat matrix. Through the absorption of fluids from the wound exudate, the fibers gradually turn into a gel pillow which retains the fluids and does not release them. The fibers are constructed such that the wound exudate is only absorbed in a vertical direction. This means that as long as the capacity is sufficient, the exudate does not flow over the edge of the wound. This allows for effectively preventing a maceration of the edge of the wound.

Said hydro-active polymers may also be alginates. Alginates are derived from brown algae, and woven into a fibrous fleece. Chemically these are polysaccharides, and specifically calcium and/or sodium salts of alginic acids. Alginates can absorb up to 20 times their own weight in fluids, the wound exudate being stored in the hollow spaces. The Ca2+ ions in the alginate grid are exchanged for the Na+ ions from the exudate until the alginate is saturated with Na+ ions. This leads to a swelling of the wound dressing and to a transformation of the alginate fibers into a gel body due to the swelling of the fibers.

Said hydro-active polymers may also be hydrogel nanoparticles, comprising hydroxy-terminated methacryllic monomers such as 2-hydroxyethyl methacrylate (HEMA) and/or 2-hydroxy-propyl methacrylate (HPMA), which are marketed as Altrazeal.

In a further preferential embodiment, the absorption element contains ≥40% by weight of super-absorbing polymers. Preferentially in particular, the weight share of the super-absorbing polymers is ≥45, 50, 55, 60, 65 or 70 percent by weight.

Preferentially in particular, the absorption element features a fleece comprising cellulose fibers.

Preferentially, the absorption element features an essentially flat absorption element made out of absorbing material, consisting of an absorbing fleece with super-absorbing polymers distributed inside it. These may come in the form of a granulate, a powder, a fill, pellets, a foam, in the form of fibers, or a fibrous fabric, mat, fleece, and/or fibrous wads.

present invention, as disclosed, for example, in WO03094813, WO2007051599, and WO0152780, and as marketed under the trade name "Sorbion Sachet". The disclosure content of the aforementioned documents is added to the disclosure content of the present document in its full scope.

In a different embodiment, the absorption element may also form a core containing—possibly flocculent—fibers or yarns made of super-absorbing polymers as well as super-absorbing polymers in granulate form, in which the granulates are glued or welded at various levels to the fibers or yarns, and in which the granulates are distributed over more than 50% of the entire height of at least one section of the core, containing areas in which granulates and fibers are mixed. Preferentially, the proportion of the super-absorbing polymers is in the range from 10 to 25% by weight. Similar constructions are known from conventional incontinence materials, and they are known for their cushioning properties similar to those of sanitary pads. Said core may be surrounded by a cover which overlaps with it in some areas, and which may cover an adhesive seam, or be part of such.

Preferentially in particular, the absorption element features a fleece, preferentially a nonwoven or airlaid, consisting of super-absorbing fibers ("SAFs", preferentially polyacrylate), or containing them as components. The fibers may be mixed with fluff pulp (cellulose) or with polyester fibers, for example, alternatively or in addition, a layered structure may be featured.

TABLE 1

| Type | 1 | 2 | 3 | 4 | 5 | 6 |
|---|---|---|---|---|---|---|
| Structure 1 | layered structure: thermo-bonded airlaid with laminated nonwoven | 40% polyester short cut fiber; 60% SAF needle felt | bicomponent fiber of a SAF and a thermoplastic material | layered structure: thermo-bonded airlaid with laminated nonwoven | 25% polyester; 75% SAF needle felt | 40% polyester short cut fiber; 60% SAF needle felt |
| Structure 2 | bicomponent fiber of a SAF and a thermoplastic material + fluff pulp | | Carded thermo-bonded nonwoven | bicomponent fiber of a SAF and a thermoplastic material + fluff pulp | | |
| SAF fiber type | 101/6/10 | 102/52/10 | 102/52/10 | 101/6/10 | | |
| Weight (g/m$^2$) | 560 | 540 | 1000 | 350 | 150 | 380 |
| Thickness (mm) | 6 | 5.4 | 20 | 3.5 | 2.4 | 3.8 |
| Absorption capacity | 31.2 l water/m$^2$ | >20 g water/g | >16 g water/g or 16,000 g water/m$^2$ | 19.5 l water/m$^2$ | >25 g 0.9% table salt/g | >17 g water/g or 6,400 g/m$^2$ |
| Absorption capacity under pressure (ml 0.9% table salt/m$^2$ at a pressure of 0.2 psi) | 16 | | | 16 | | |
| Total content of super-absorbing polymers (% w/w) | 18 | 40 | 50 | 18 | 75 | 60 |
| Tensile strength (N/5 cm) | | | | | 16 ± 13 | 16 ± 13 |
| Elasticity (%) | | | | | 60 ± 18 | 60 ± 18 |

The absorption element features at least one material selected from the group containing a mat, in particular an airlaid made of said yarns or fibers of super-absorbing polymers with super-absorbing polymers worked in, and/or a loose filling of super-absorbing polymers. Preferentially, said airlaid mat features an essentially flat material section made of absorbing material, consisting, for instance, of an absorbing fleece from the aforementioned fibers with super-absorbing polymers worked into them.

This absorption element may correspond to the absorbing insert included in a wound dressing of the Applicant of the In another embodiment, the absorption element may also contain at least one flat layer comprising fibers or yarns made of super-absorbing polymers, onto which super-absorbing polymers in granulate form are glued. This leads to a preferential embodiment of a structure of the body which comprises at least three layers, in which two cover layers surround one layer comprising super-absorbing polymers.

Herein, there is no mixture of fibers and super-absorbing polymers on one level, but merely an adjacent positioning of the two materials. In a preferential embodiment, the additional layers, if provided, may also have been physically compacted with each other by means of rolling, pressing, calendaring, or a similar procedure.

TABLE 2

| Type | 1 | 2 | 3 | 4 | 5 | 6 | 7 | 8 |
|---|---|---|---|---|---|---|---|---|
| Weight (g/m$^2$) | 450 | 300 | 150 | 50 | 100 | 120 | 140 | 440 |
| Thickness (mm) | 1.3 | 1.2 | 0.9 | 0.7 | 0.7 | 0.76 | 1 | 1.2 |
| Fluidity retention (g/g) | 28 | 33 | 28 | 15 | 25 | 28 | 11.5 | 38 |
| Tensile strength (n/5 cm) | 25 | 55 | 20 | 20 | 20 | 20 | 15 | 20 |
| Absorption capacity (g/g) | 45 | 20 | 50 | 20 | 40 | 50 | 28 | 55 |

Moreover, the body may feature repetitive patterns or textures, such as a checked pattern, a punched pattern, etc.

Preferentially in particular, said absorption element has features surface dimensions of 5×5, 5×10, 5×20, 10×10, 10×15, 10×20, 15×15, 20×20, or 20×40 cm.

Preferentially in particular, said absorption element comprises at least a second adjacent layer in addition to the layer comprising super-absorbing polymers, which contains no or fewer super-absorbing polymers, and the surface of which extends beyond the former layer. In this way it can be ensured that the layer comprising super-absorbing polymers can gain in volume as a result of its absorption of fluids without that volume increase being visible from the outside, because this layer is concealed by the second layer.

The foam materials may be foam materials with closed or with open pores. Preferentially, these materials are embodied as flat layers as well, featuring fluid-absorbing properties on the one hand and cushioning properties on the other hand. They are further characterized by high restoring forces.

Preferentially in particular foams of the type known as cold foams are used.

As an alternative or in addition to said foams, so-called "nanofiber matrices" such as those produced by the SNS Nano Fiber company may be used as well.

Furthermore, said foams may also contain super-absorbers such as the Allevyn Plus product of the Smith & Nephew company.

Further preferentially, the device also contains a wound-facing wound contact lattice permeable to fluids.

Preferentially, such a wound contact lattice is a lattice made of a synthetic material (preferentially comprising, for example, a silicone material or a nylon material), a perforated foam material, a spacer fabric, and/or a perforated foil.

Preferentially, a three-dimensional wound contact lattice is provided, such as the one marketed under the trade name of "Sorbion Plus" and described in EP2004116A1.

The wound contact lattice may be positioned on the wound-facing side on the one hand, either loosely inside the frame or fixed to the frame.

Such a wound contact lattice prevents granulation and therefore allows for a non-traumatic wound dressing change. It further has a biofilm-dissolving effect as well as a valve effect, through which the return flow of exudate is reduced.

The Applicant was able to demonstrate that these properties, which are known from "passive" wound dressings, are also especially advantageous for the "active" vacuum-supported wound dressings described here.

The wound contact lattice may also be positioned on the cover side. This way it may prevent gel blocking that may be caused by an interjacent absorption element comprising super-absorbing polymers when these form a gel as a result of the absorption of fluids which otherwise would possibly impede the fluid suctioning process.

In principle, the aforementioned connection device for the suctioning of fluid media can be embodied so as to allow the suctioning of fluids and/or gases. For these purposes, it may be embodied in the form of a coupling (such as in the Luer-Lock system) which allows for the connection of a hose and/or a pump.

The product may further comprise an additional valve, a pressure reducer or even an additional window that can be opened. These make it possible for the device to be used even with an excessively strong negative pressure, for example when [connected to] a vacuum wall port, which can be frequently found in hospitals. Said valve, pressure reducer or window can then be opened in order to reduce the negative pressure.

Further preferentially, a barrier is located in the region of the connection device for the suctioning of fluid media that is impermeable to fluids.

This is to ensure that no fluids enter into the pump. The latter remains inside the wound covering and is absorbed by the wound exudate-extracting absorption element.

Preferentially, said barrier comprises a semi-permeable membrane, for example one made out of a material such as Goretex, etc.

Preferentially, one connection device for the suctioning of fluid media and one connection device for the suctioning of gaseous media can be provided.

Further preferentially, the device also comprises a facility for the generation of atmospheric negative pressure.

Said facility for the generation of atmospheric negative pressure is preferentially selected from the group comprising: a) electrically operated vacuum pump; b) manually operated negative pressure source, and/or c) evacuated vacuum vessel.

Said vacuum pump may be a solitary pump, but it may also be part of a centralized vacuuming system as often used in clinics. Hospital rooms are often fitted with vacuum wall ports to which the invented drainage devices for wound treatment can be connected. In this case, said vacuum pump can apply negative pressure to a plurality of drainage devices for wound treatment according to the invention.

Preferentially this is a micro-pump of which the dimensions and/or weight are such that they can be applied without difficulty to a wound-covering element of the aforementioned type, without bothering the patient or hindering him in any way.

For example, this pump may be a piezo- or membrane pump. Preferential in particular are piezo-pumps, which are pumps whose pumping capacity is brought about by a piezo-electrical element. These pumps have a sufficiently high pumping capacity despite its small dimensions. They further have low operating noise and low energy consumption. Alternatively, the pumps may also be a microsystems technology propellant-driven vacuum pump. Suitable pumps of this type are manufactured, for example, by Schwarzer Precision, KNF, or Bartels Mikrotechnik.

Preferentially, such a pump is equipped with a check valve, which allows for the pump to be operated in interval mode, or only for the initial generation of negative pressure, or only in order to maintain negative pressure, without the occurrence of leaks during the operating pauses which would reduce the built-up negative pressure again.

Preferentially, said pump is capable of generating negative pressures of −60 to −200 mm Hg. Preferentially in particular, the pump is capable of generating negative pressures of −60, 70, 80, 85, −90, −100, −110, −120, −130, −140, −150, −160, −170, −180, −190 or −200 mm Hg.

Preferentially, the pump is selected or equipped such that it is capable of transporting fluids.

Preferentially, the operating noise of the pump does not exceed the acoustic pressure level of 65 dB. preferentially in particular, the acoustic pressure level of 63 dB, 60 dB, 58 dB, 55 dB, 53 dB, 50 dB, 48 dB, 45 dB, 42 dB, 40 dB, 38 dB, 35 dB, 32 dB, 30 dB, 28 dB, 25 dB, 22 dB, or even 20 dB is not exceeded.

Preferentially, the pump features a transportation rate of between 0.5 ml min$^{-1}$ and 100 ml min$^{-1}$. Preferentially the transportation rate is between 2 ml min$^{-1}$ and 50 ml min$^{-1}$. Preferential in particular are transportation rates between 10 ml min$^{-1}$ and 20 ml min$^{-1}$.

The aforementioned evacuated vessel can be connected to the invented device for wound treatment in a manner similar to that of the previously known Redon bottle, and so apply negative pressure to it. Said evacuated vessel comprises an insert containing a fluid-absorbing polymer, preferentially in the form of a lining.

Preferentially in particular, said evacuated vessel can be embodied in the form of a cartridge, which is positioned in a mount which is already connected with the invented drainage device for wound treatment. When the cartridge is full, it can be removed and disposed of, and a new evacuated cartridge can be placed in the mount.

The aforementioned embodiments are particularly advantageous, because they dispense with the need for a pump of their own, and instead use an evacuated vessel which makes the device mobile and independent of the power grid, with as a result that the patient himself becomes mobile. Moreover, this allows for a smaller construction which allows the patient to discretely conceal the device. Particularly advantageous in this respect is an anatomically adjusted embodiment of said evacuated vessel or mount, which allows for an inconspicuous carrying thereof, for instance on the leg.

Moreover, such a device produces no operating noises, and is very easy to operate.

The same applies to the aforementioned manually operated negative pressure source. In the most simple embodiment, this may be a plastic syringe with a sufficiently high volume. Other options are a pump shaped as a rubber ball, bellows, etc.

Further preferentially, the facility for the generation of atmospheric negative pressure is positioned directly on the wound care device.

This may be accomplished, for example, by positioning said facility directly onto the wound-covering element. In this way, a separate vacuum hose, which involves manufacturing challenges (sufficient rigidity in order not to collapse under vacuum conditions) as well as hygienic problems (risk of contamination) can be eliminated, or be kept very short.

Further preferentially, a coupling, a blocking valve, and/or a three-way valve is positioned between the facility for the generation of atmospheric negative pressure and the wound-covering element or the wound exudate-extracting absorption element.

This device allows for ensuring that a) the facility for the generation of atmospheric negative pressure can be disconnected from the test of the device, b) a once generated negative pressure can be retained for the longest possible time, and/or c) in order to spare the battery or when the battery is empty, an external pump or an external vacuum vessel can be used to generate or restore negative pressure.

Said external pump or said external vacuum vessel may be stationary in the clinic or in the patient's home, for example, but it may also be embodied in a mobile form (for example in the form of a suitcase, or integrated in the patient's clothing, or attached to the patient's belt). This is to ensure that the device on the wound remains small and inconspicuous, since its primary task is to maintain the vacuum, but to provide sufficient pumping capacity when needed in order to allow for an efficient therapy.

Further preferentially, the absorption element is surrounded by a cover permeable to fluids. Preferentially, the device further comprises a spacer. Preferentially, this spacer is positioned between the wound and the wound-covering element, but also, if applicable, between the absorption element and the wound-covering element, or between the wound and absorption element placed. Such a spacer ensures that the wound care device does not collapse entirely when negative pressures is applied, since this would result in an inability to extract gases or fluids.

Further preferentially, the device features a layer comprising a heavy metal, preferentially copper or silver, or a salt containing one of these. Specifically in cases of an extended application period on the wound, such a layer can be very helpful, as it slows down the growth of bacteria.

Further preferentially, the wound-covering element is impermeable to fluids and/or gases. This allows for the application of a vacuum, and it prevents the leakage of fluids, which may in the circumstances be contaminated.

Preferentially, said wound-covering element is embodied of an elastic material. For these purposes, it may, for example, consist of polypropylene, polyethylene, latex, silicone, or rubber. Furthermore, it may be fitted on the inside with a foam material.

Further preferentially, the wound-covering element is permeable to water vapors. Preferentially, the wound-covering element is further embodied in a transparent manner.

Further preferentially, the pumping direction of the facility for the generation of atmospheric negative pressure is reversible. This allows for the use of the facility as a controllable dosing pump for medications, rinsing solutions, etc.

Further preferentially, said window that can be opened features a non-elastic back panel. The "back panel" concept here means the cover as such, as shown, for example by reference no. 23. In this embodiment, for example, the aforementioned pump can be positioned directly on the back panel of the window that can be opened.

Further preferentially, said window that can be opened features an elastic back panel. In this embodiment, for example the back panel may be embodied so as to yield to the volume increase of an underlying absorption element that is caused as a result of exudate absorption.

This also allows ensuring that the window follows the movements of the patient in order to guarantee tightness.

Preferentially, this elastic back panel features a silicone material, or is made out of such a material. Preferentially in particular, for example, the lower side of the back panel, in other words, the patient-facing side, is coated with a silicone and/or foam material, or lying on top of such a material.

Further preferentially, said window that can be opened features a back panel made of a plastic malleable material.

In this embodiment, for example, the back panel may consist of a thermoplastically malleable deep draw foil. This allows for the creation of a reservoir in which, for example, a reserve absorption element may be provided.

Preferential is further the application of a wound care device for the treatment of wounds comprising soft tissue defects, infected wounds after surgical debridement, lymphatic fistulae, sternal wound infections, thoracic wall ports, pressure sores, venous ulcers, chronic wound healing disorders, radiation ulcers, abdominal compartment syndrome, septic abdomen, enteral fistulae, and/or wounds caused by one or several edemas, for fixing skin transplants, for wound conditioning, and/or for post-operative care of sutures and incisions.

Furthermore, the application of a wound care device according to one of the previous claims in a wound compression system is devised.

FIG. 1 shows the general principle of a wound care device for the treatment of wounds by means of atmospheric negative pressure in the wound region, comprising a wound-covering element 3 that can be attached to the skin of a patient, as well as a connection device (not shown) for the suctioning of fluid media. The wound-covering element features a window that can be opened 23, which is positioned by means of a gas-tight closure (not shown) on the wound-covering element. After the opening of the windows 23, a wound dressing 2 can be easily removed, disposed of, and replaced by another wound dressing.

Figure 2:
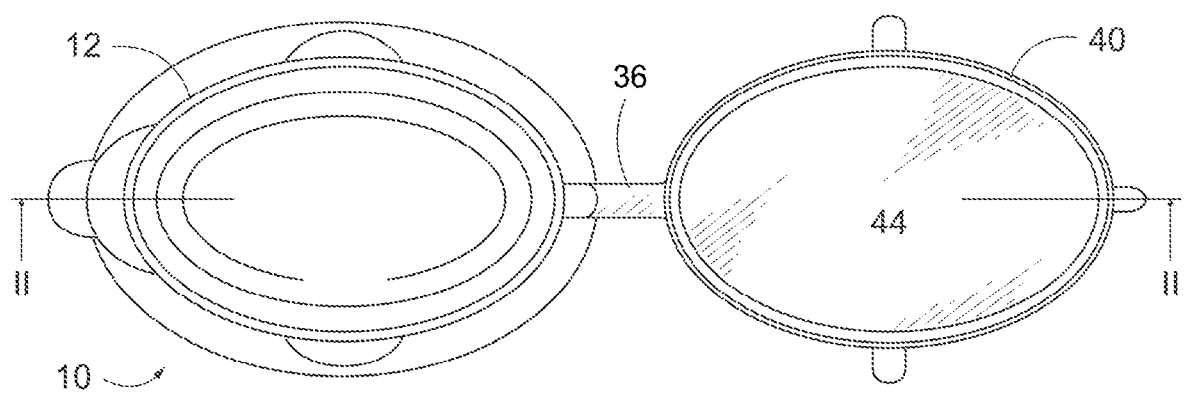
FIG. 2 is a top view of a window that can be opened 10, comprising a frame 12, a connecting strap 36 between frame 12 and window cover 46, according to one embodiment.

FIG. 2 shows a window that can be opened 10, comprising a frame 12, a connecting strap 36 between frame 12 and window cover 46, as well as a gas-tight closure embodied as an interlocking seal 18, 40.

Figure 3:
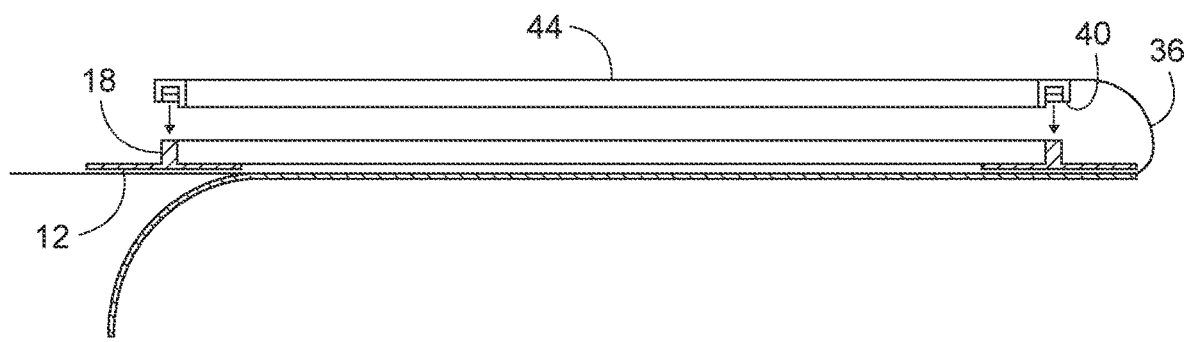
FIG. 3, a cross-sectional view of the interlocking seal 18, 40, according to one embodiment.

In FIG. 3, a cross-section of said interlocking seal 18, 40 is shown in detail.

FIG. 4 also shows a window that can be opened with an interlocking seal 42, 43. The aforementioned interlocking seal features a tongue and groove option, which ensures that the closing or opening of the interlocking seal requires only a low degree of force. In this way, the opening or closing can be performed without exposure [of the patient] to pain. Furthermore, the seal is characterized by a low height and a low weight.

Figure 5A:
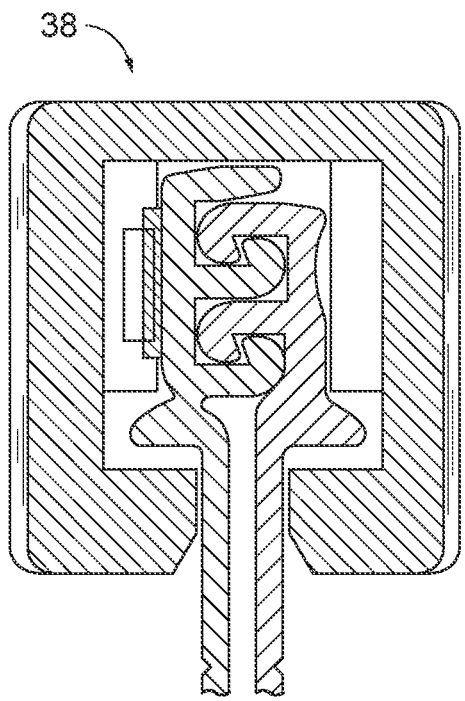
FIG. 5a is a top cross-sectional view of the interlocking seal according to another embodiment, in the form of a slider 38 that slides along to lips that are to be sealed similar to a zipper, and moves them into the sealed position.

FIG. 5a shows a different form of the interlocking seal that can be used with the invention, in the form of a slider 38 that slides along to lips that are to be sealed similar to a zipper, and moves them into the sealed position.

Figure 5B:
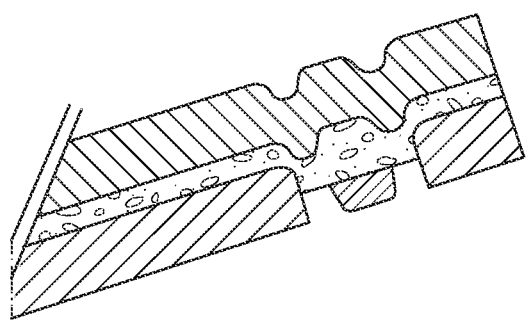
FIG. 5b is a side cross-sectional view of a gas-tight closure in the form of an adhesive seal.
Figure 5B:
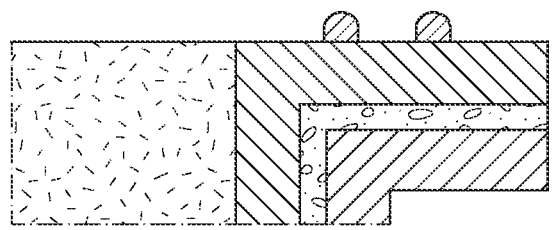

FIG. 5b shows a gas-tight closure in the form of an adhesive seal.

Figure 6A:
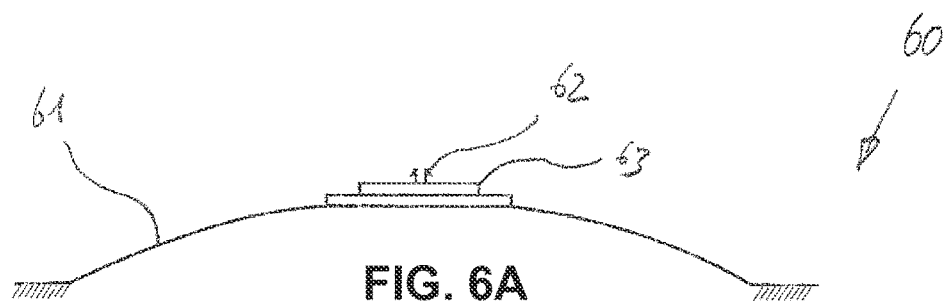
FIG. 6a is a side view of a wound care device according to another embodiment for the treatment of wounds by means of atmospheric negative pressure in the wound region, comprising a wound-covering element 61 that can be attached to the skin of a patient, as well as a connection device 62 for the suctioning of fluid media.
Figure 6B:
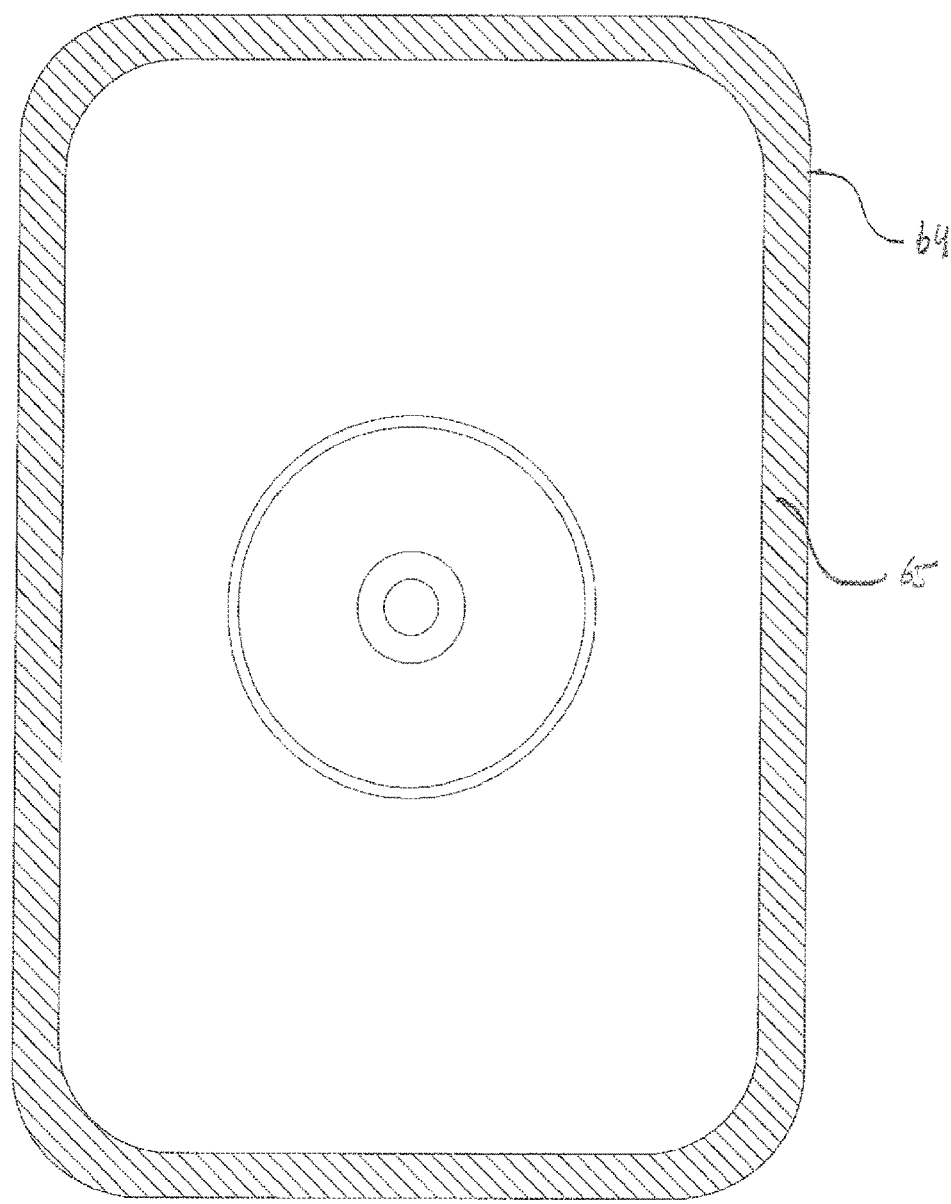
FIG. 6*b* is a top view of the wound-covering element shown in FIG. 6*a*.

FIG. 6 shows a wound care device 60 for the treatment of wounds by means of atmospheric negative pressure in the wound region, comprising a wound-covering element 61 that can be attached to the skin of a patient, as well as a connection device 62 for the suctioning of fluid media. The wound-covering element features a window that can be opened 63, which is positioned by means of a gas-tight closure on the wound-covering element.

The wound-covering element further features a surrounding border 64 comprising an adhesive material 65. This is an implementation of a so-called "border dressing".

Figure 7:
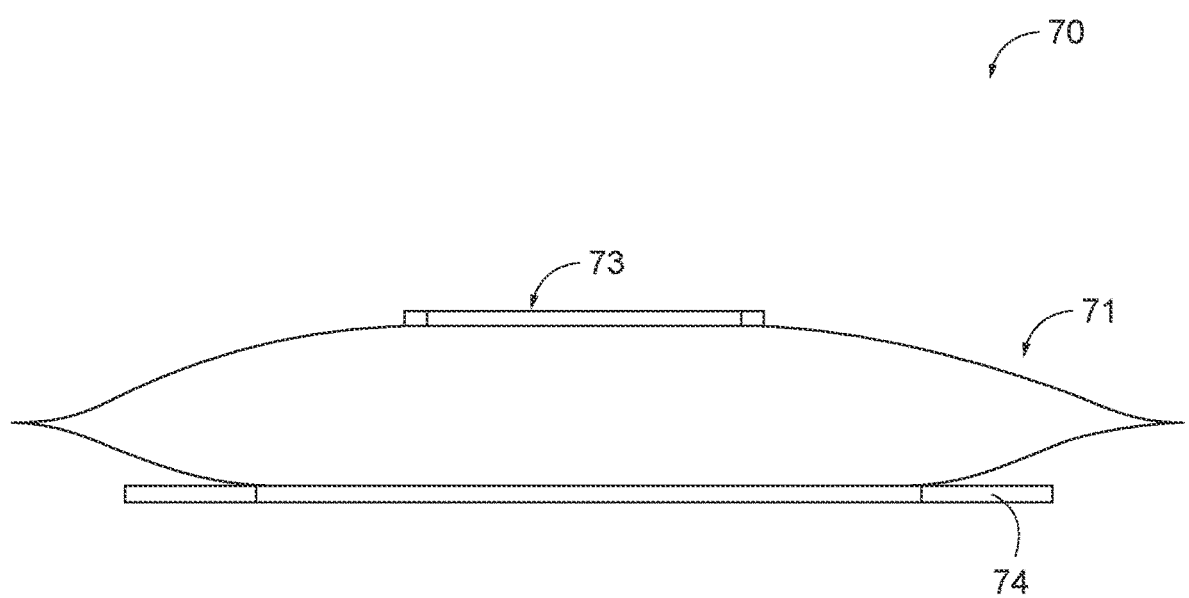
FIG. 7 is a side view of a wound care device according to another embodiment for the treatment of wounds by means of atmospheric negative pressure in the wound region, comprising a wound-covering element 71 that can be attached to the skin of a patient, as well as a connection device (now shown) for the suctioning of fluid media.

FIG. 7 shows a wound care device 70 for the treatment of wounds by means of atmospheric negative pressure in the wound region, comprising a wound-covering element 71 that can be attached to the skin of a patient, as well as a connection device (now shown) for the suctioning of fluid media. The wound-covering element features a window that can be opened 73, which is positioned on the wound-covering element by means of a gas-tight closure.

The device further features a panel or a frame 74, onto which the wound-covering element is distally positioned. In this embodiment, said panel or strip may feature a central opening, for example, which is positioned over the wound. In this embodiment, said panel or strip takes the form of a frame. Alternatively, said panel or strip may be embodied such that a window may be cut into the panel or the strip, corresponding in shape to the outline of the wound. Said panel might consist, for example, of the hydrocolloid material described herein. Said strip consists, for example of an incision foil as described above, which is a self-adhesive foil made out of a polymer material.

Figure 8:
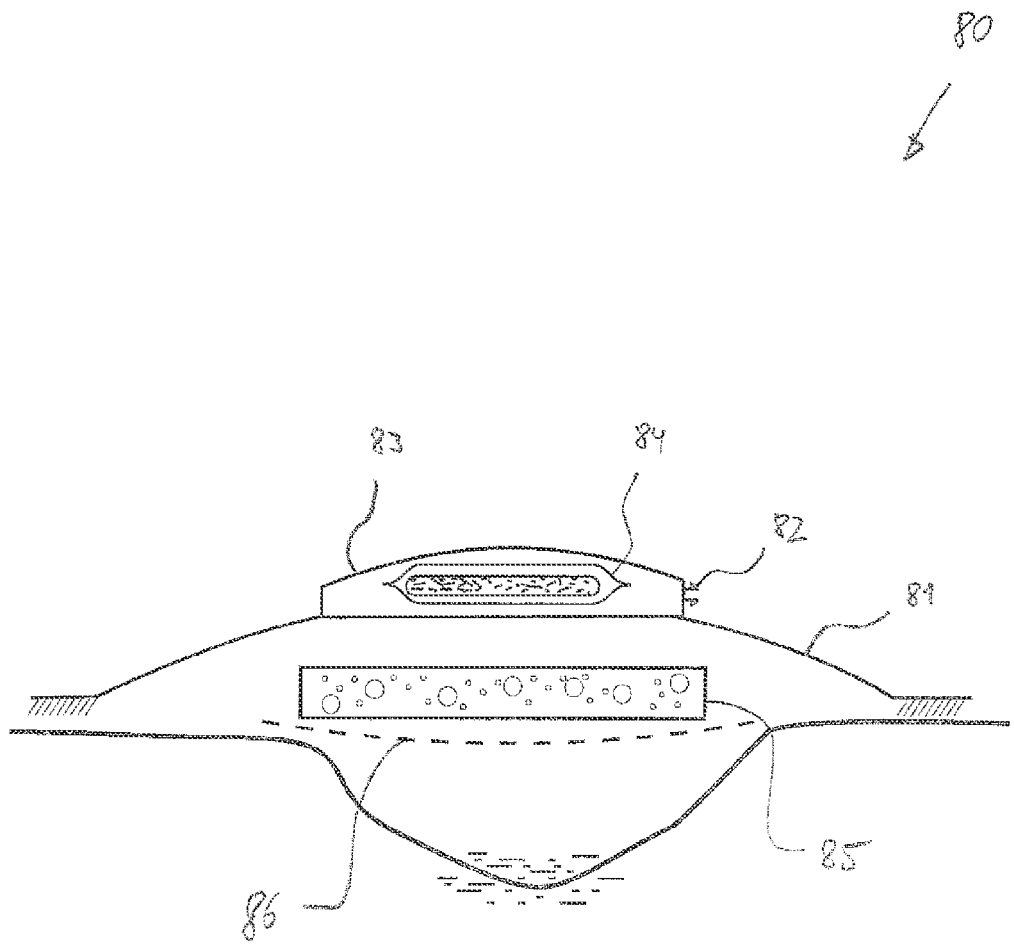
FIG. 8 is a side view of a wound care device according another embodiment for the treatment of wounds by means of atmospheric negative pressure in the wound region, comprising a wound-covering element 81 that can be attached to the skin of a patient, as well as a connection device 82 for the suctioning of fluid media.

FIG. 8 shows a wound care device 80 for the treatment of wounds by means of atmospheric negative pressure in the wound region, comprising a wound-covering element 81 that can be attached to the skin of a patient, as well as a connection device 82 for the suctioning of fluid media. The wound-covering element features a window that can be opened 83, which is positioned on the wound-covering element by means of a gas-tight closure.

The window that can be opened is fitted with a pressure-resistant lining, and offers room for an absorption element 84 comprising super-absorbing polymers. Due to the resistance to pressure, the window that can be opened does not collapse, so that the absorption element can utilize its full absorption capacity.

Furthermore, a continuous body 85 made of a foam material, as well as a three-dimensional wound contact lattice 86 are provided on the wound-facing side.

Figure 9A:
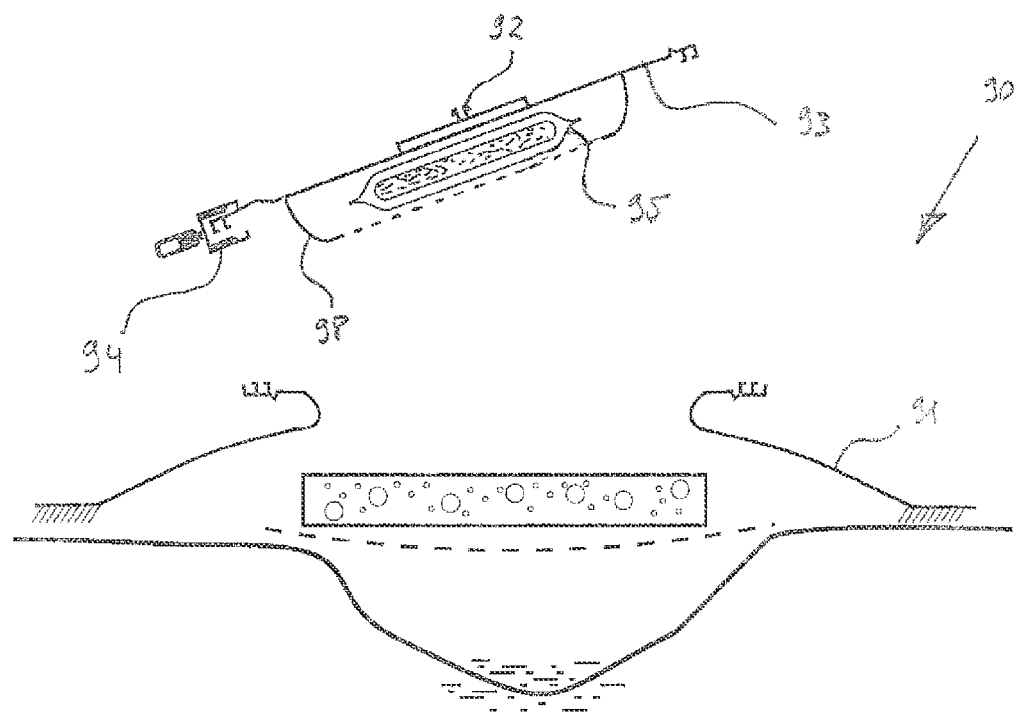
FIG. 9*a* is a side view of a wound care device according to another embodiment for the treatment of wounds by means of atmospheric negative pressure in the wound region, comprising a wound-covering element 91 that can be attached to the skin of a patient, as well as a connection device 92 for the suctioning of fluid media.
Figure 9B:
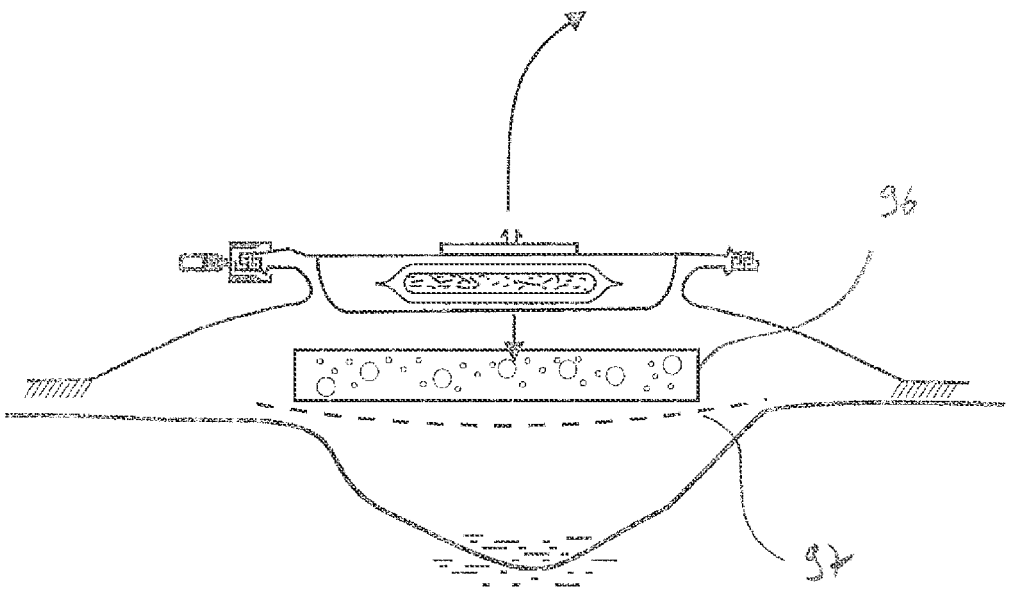
FIG. 9*b* is a side view of the wound care device shown in FIG. 9*a* being attached to the skin of a patient.

FIG. 9 shows a wound care device 90 for the treatment of wounds by means of atmospheric negative pressure in the wound region, comprising a wound-covering element 91 that can be attached to the skin of a patient, as well as a connection device 92 for the suctioning of fluid media.

The wound-covering element features a window that can be opened 93, which is positioned on the wound-covering element by means of a gas-tight interlocking seal 94. The aforementioned interlocking seals are also known under the pseudonyms of "Ziplock", "Minigrip", or sliding closure. They have a low height and a low weight, and they require only a small degree of force for closing or opening them.

Underneath the window that can be opened 93, a compartment 98 with a pressure-resistant lining is devised, which offers room for an absorption element 95 comprising super-absorbing polymers. Said compartment is embodied on the wound-facing side as being permeable to fluids. Due to the resistance to pressure, the window that can be opened does not collapse, so that the absorption element can utilize its full absorption capacity. When this capacity is reached, the entire window including the compartment and the absorption element contained therein can be disposed of, and replaced with a new one.

Furthermore, a continuous body 96 made of a foam material, as well as a three-dimensional wound contact lattice 97 are provided on the wound-facing side. The continuous body, other than the compartment 98, is not resistant to pressure, and therefore loses volume when pressure increases.

Figure 10A:
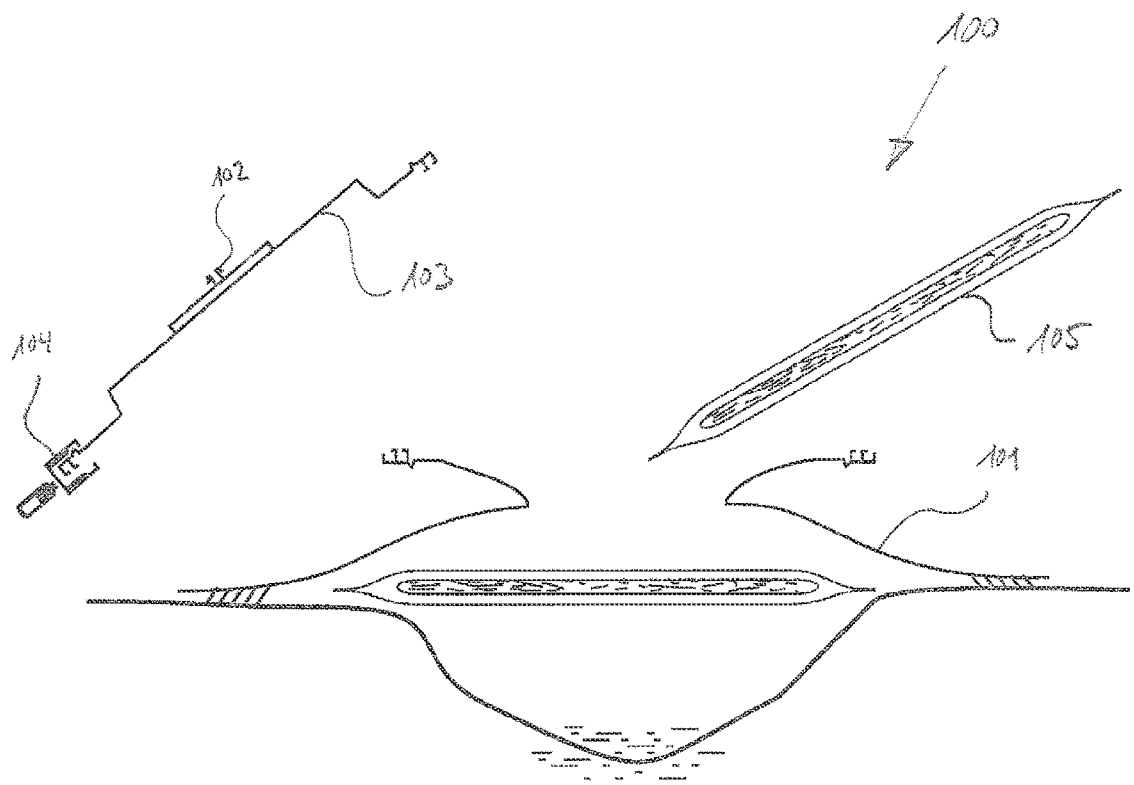
FIG. 10*a* is a side view of a wound care device according to another embodiment for the treatment of wounds by means of atmospheric negative pressure in the wound region, comprising a wound-covering element 101 that can be attached to the skin of a patient, as well as a connection device 102 for the suctioning of fluid media.
Figure 10B:
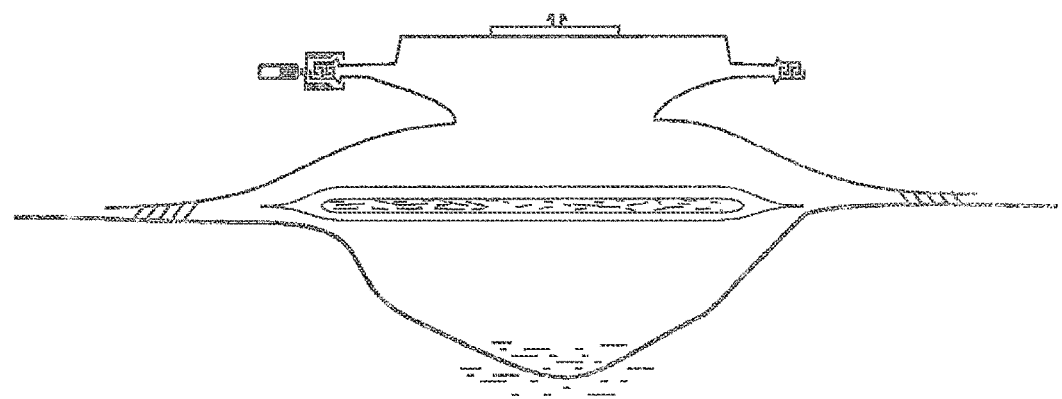
FIG. 10*b* is a side view of the wound care device shown in FIG. 10*a* being attached to the skin of a patient.

FIG. 10 shows a wound care device 100 for the treatment of wounds by means of atmospheric negative pressure in the wound region, comprising a wound-covering element 101 that can be attached to the skin of a patient, as well as a connection device 102 for the suctioning of fluid media.

The wound-covering element features a window that can be opened 103, which is positioned on the wound-covering element by means of a gas-tight interlocking seal 104. The aforementioned interlocking seals are also known under the pseudonyms of "Ziplock", "Minigrip", or sliding closure. They have a low height and a low weight, and they require only a small degree of force for closing or opening them.

Furthermore, an absorption element 105 is devised, which can be removed or inserted after the opening of the window.

Figure 11A:
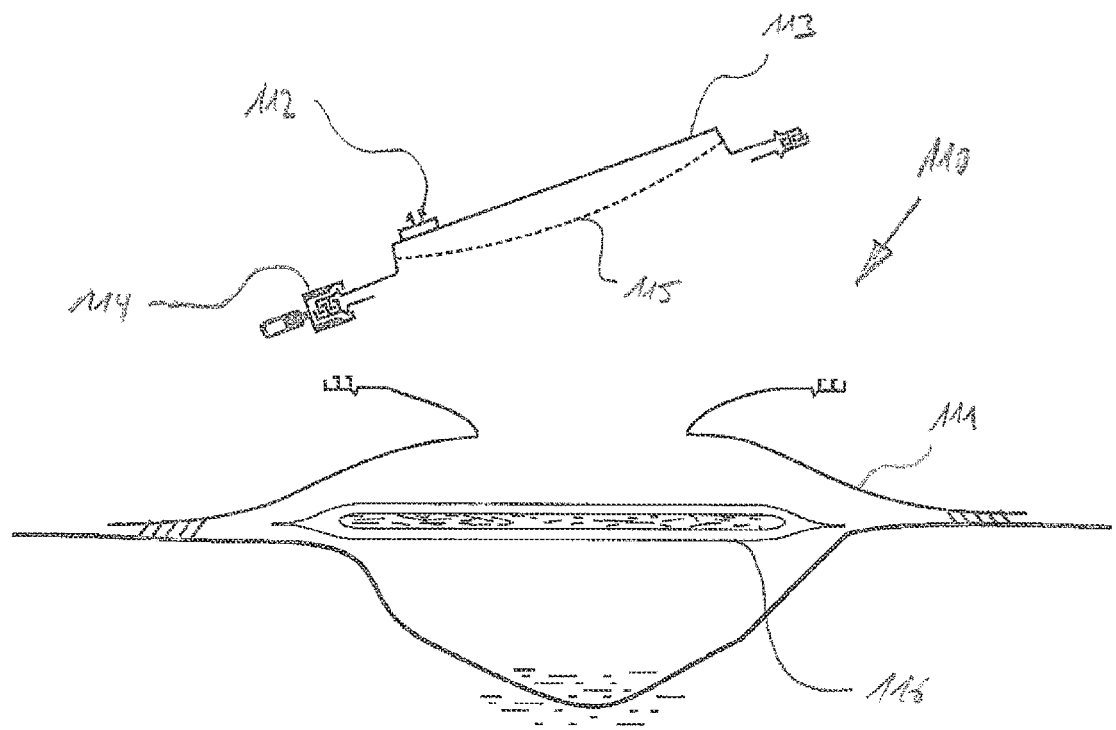
FIG. 11*a* shows a wound care device according to another embodiment for the treatment of wounds by means of atmospheric negative pressure in the wound region, comprising a wound-covering element 111, that can be attached to the skin of a patient, as well as a connection device 112 for the suctioning of fluid media.

FIG. 11a shows a wound care device 110 for the treatment of wounds by means of atmospheric negative pressure in the wound region, comprising a wound-covering element 111, that can be attached to the skin of a patient, as well as a connection device 112 for the suctioning of fluid media.

The wound-covering element features a window that can be opened 113, which is positioned on the wound-covering element by means of a gas-tight interlocking seal 114. The aforementioned interlocking seals are also known under the pseudonyms of "Ziplock", "Minigrip", or sliding closure. They have a low height and a low weight, and they require only a small degree of force for closing or opening them.

Underneath the window that can be opened 113, a lattice 115 is provided, which provides room for an absorption element (not shown), which may, for example, comprise super-absorbing polymers. The aforementioned absorption element can be placed in the lattice, after which the window that can be opened can be attached to the covering element by means of the interlocking seal. After the window is reopened, the absorption element can be removed and disposed of or replaced, for instance after having reached its full absorption capacity.

Furthermore, an additional absorption element 116 is provided on the wound-facing side, which may feature a lower degree of fluids retention than the previously mentioned absorption element.

Figure 11B:
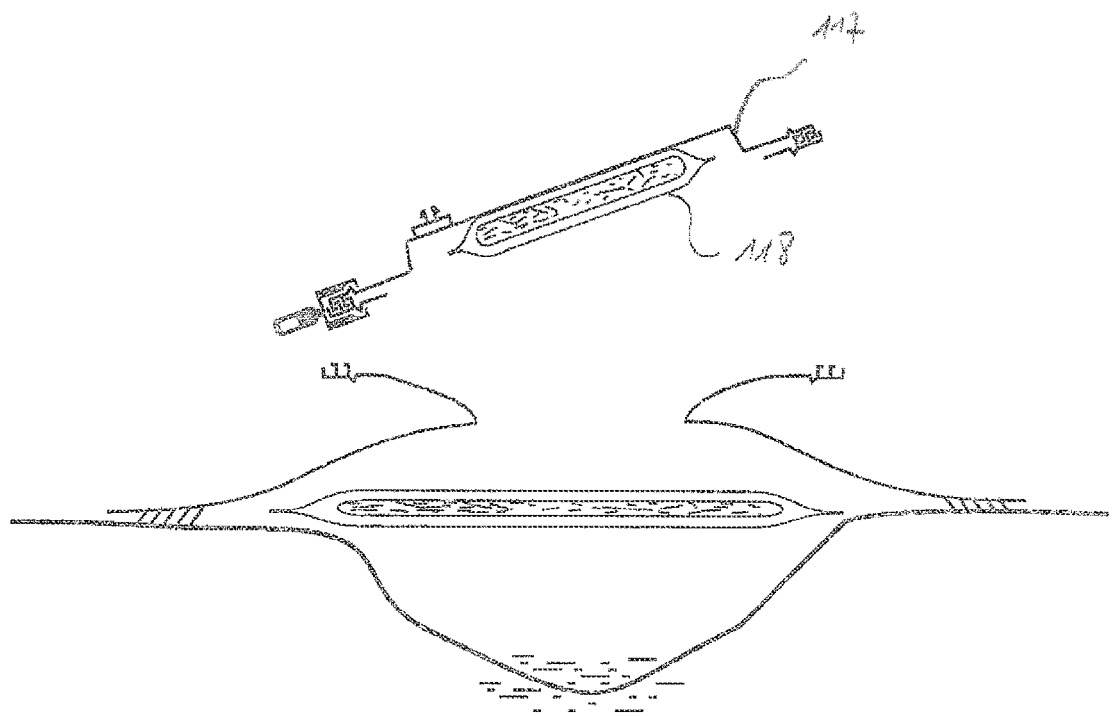
FIG. 11*b* is a side view of a device similar to the one in FIG. 11*a*, but different in that an absorption element 118 is attached to the window that can be opened 117 on the wound-facing side.

FIG. 11b features a device similar to the one in FIG. 11a, but different in that an absorption element 118 is attached to the window that can be opened 117 on the wound-facing side. When the absorption element 118 has reached its full absorption capacity, the entire window, including the absorption element attached to it, can be disposed of, and replaced with a new one.

Figure 12:
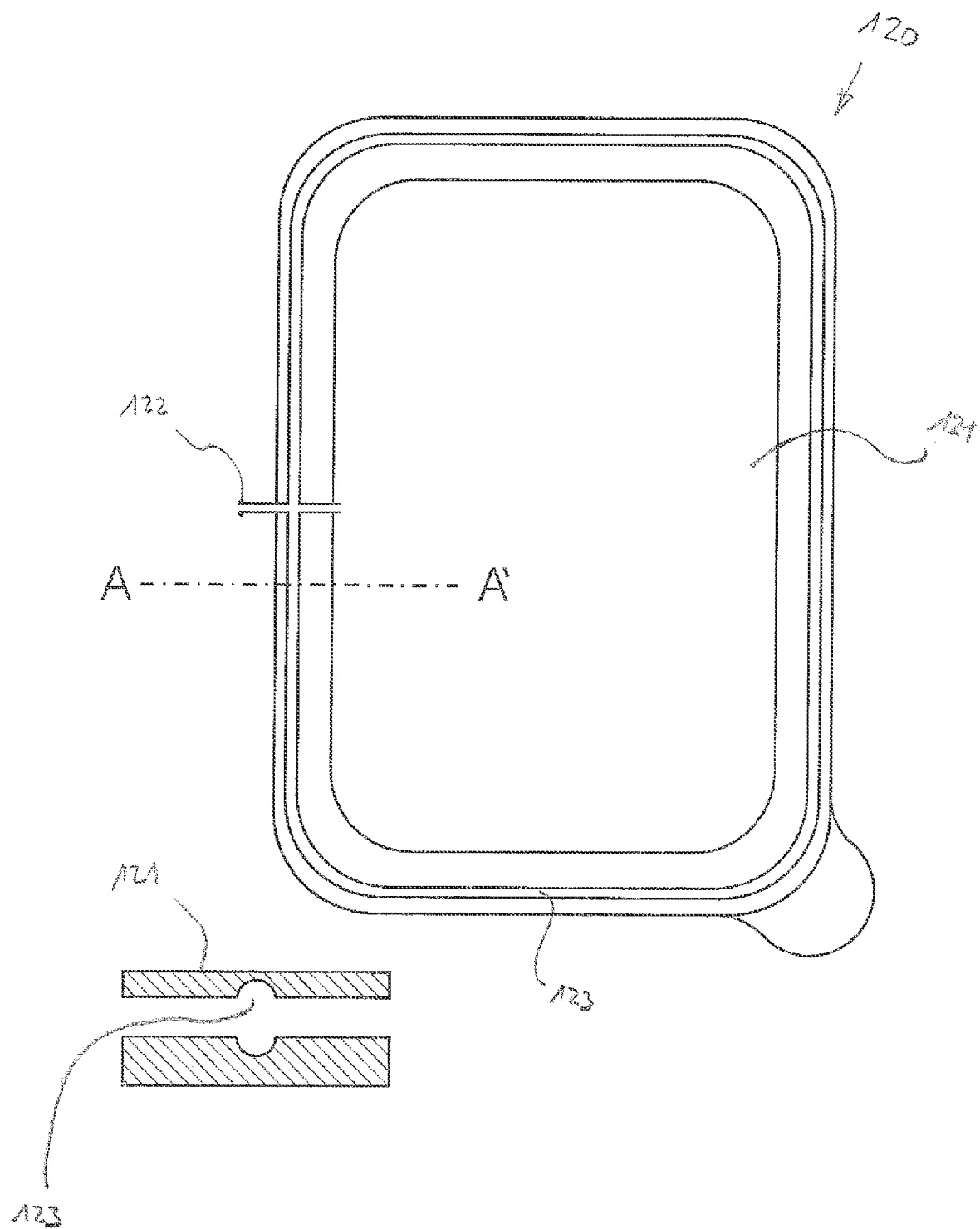
FIG. 12 is a top view of a wound care device according to another embodiment for the treatment of wounds by means of atmospheric negative pressure in the wound region, comprising a wound-covering element that can be attached to the skin of a patient, as well as a connection device 122 for the suctioning of fluid media.

FIG. 12 shows a wound care device 120 for the treatment of wounds by means of atmospheric negative pressure in the wound region, comprising a wound-covering element that can be attached to the skin of a patient, as well as a connection device 122 for the suctioning of fluid media.

The wound-covering element features a window that can be opened 121, which is positioned on the wound-covering element by means of a surrounding evacuable duct 123.

Figure 13:
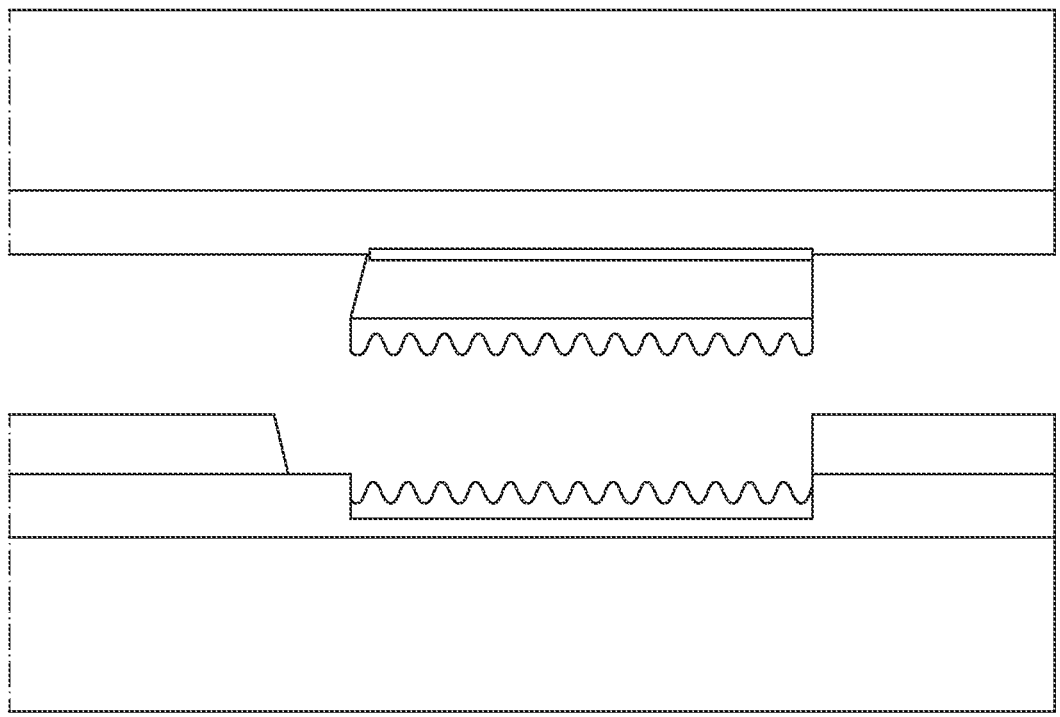
FIG. 13 is a side view of a further embodiment of a gas-tight closure in the form of an adhesive seal.

FIG. 13 shows a further embodiment of a gas-tight closure in the form of an adhesive seal.

Figure 14A:
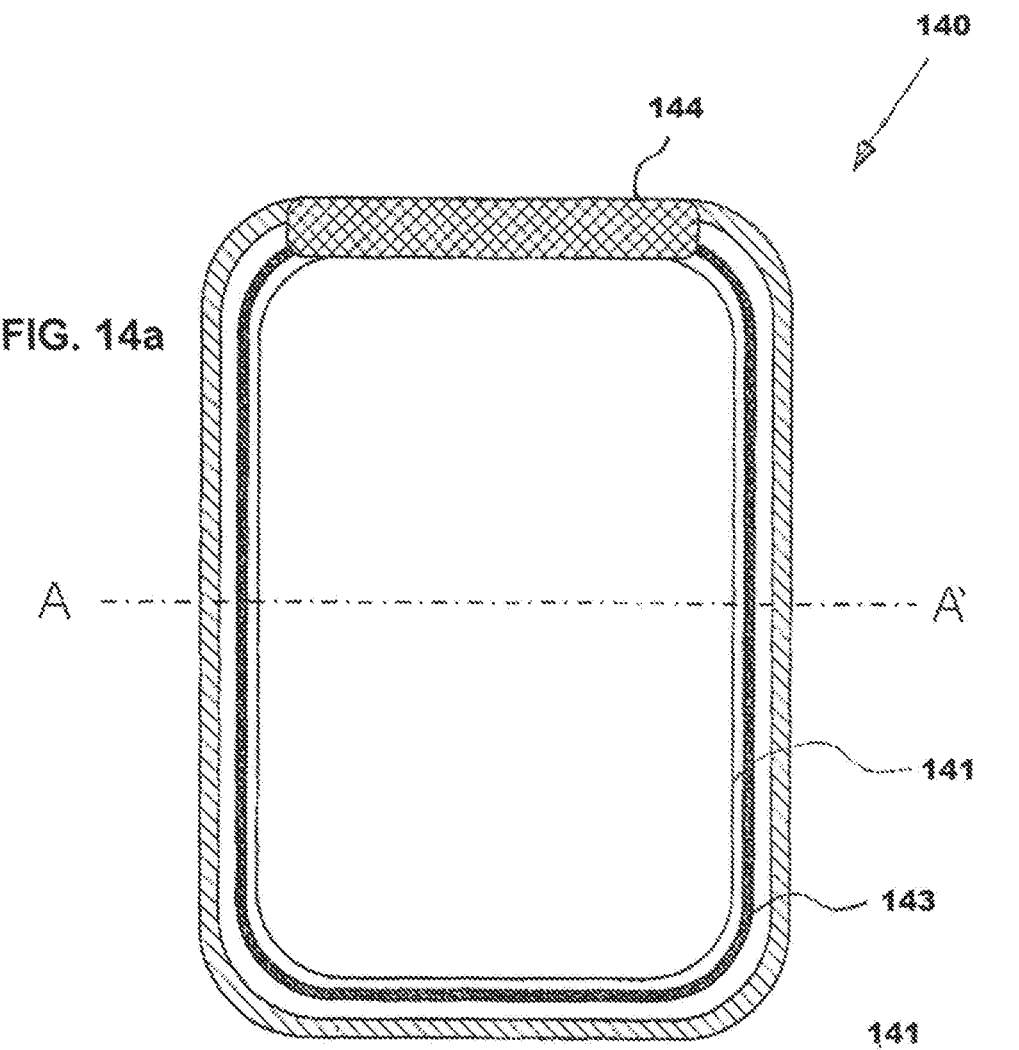
FIG. 14*a* is a top view showing a wound care device according another embodiment for the treatment of wounds by means of atmospheric negative pressure in the wound region, comprising a wound-covering element that can be attached to the skin of a patient and a connection device (not shown) for the suctioning of fluid media.
Figure 14B:
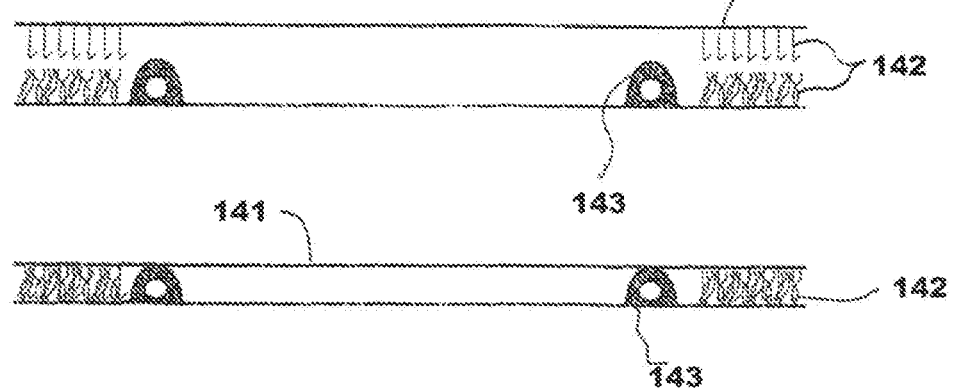
FIG. 14*b* is a side view taken along line A-A from FIG. 14*a*.

FIG. 14 shows a wound care device 140 for the treatment of wounds by means of atmospheric negative pressure in the wound region, comprising a wound-covering element that can be attached to the skin of a patient and a connection device (not shown) for the suctioning of fluid media.

The wound-covering element features a window that can be opened 141, which can be attached to the wound-covering element by means of a tongue and groove seal 142. Furthermore, a surrounding rubber tube 143 is provided in the middle, which is compressed by the tongue and groove seal, producing a gas-tight closure. As an alternative to the rubber tube, a rubber seal, a cork strip or something similar can be provided.

Furthermore, a hinge 144 is provided, which connects the window that can be opened on one side with the wound-covering element, so that the latter can be folded back, but not be removed entirely.

Figure 15A:
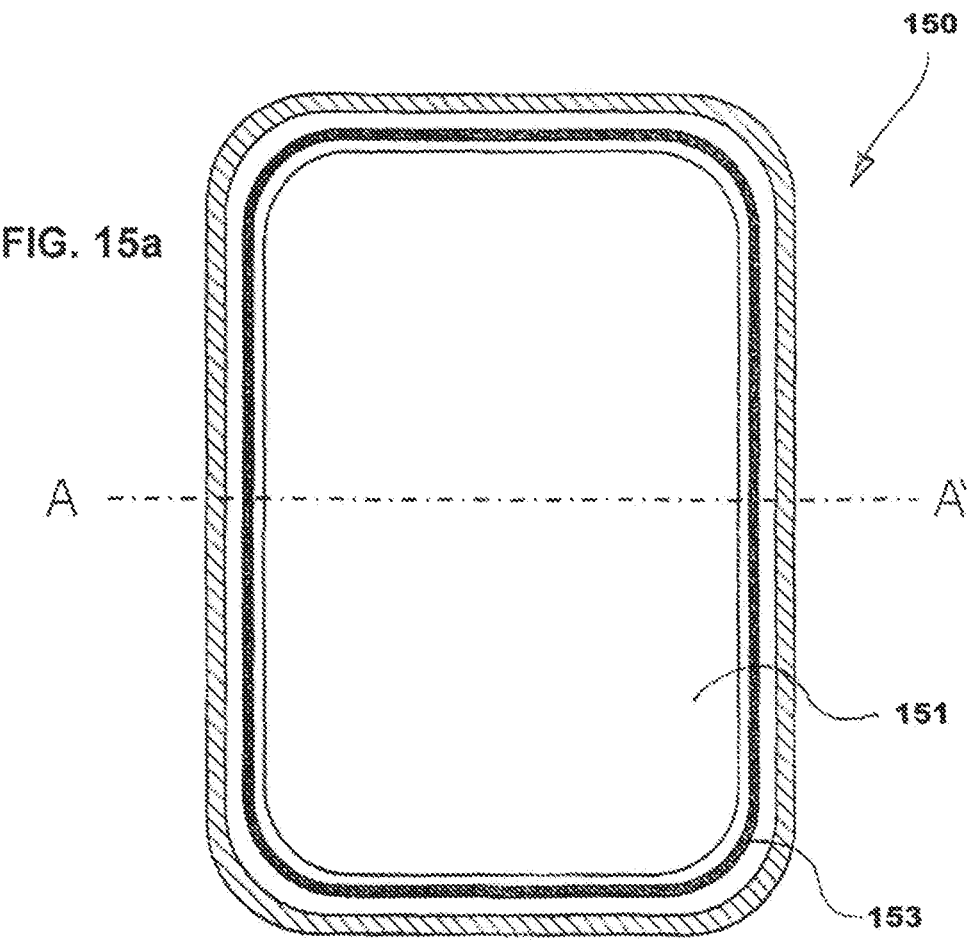
FIG. 15*a* is a top view showing a wound care device according another embodiment for the treatment of wounds by means of atmospheric negative pressure in the wound region, comprising a wound-covering element that can be attached to the skin of a patient and a connection device (not shown) for the suctioning of fluid media.
Figure 15B:
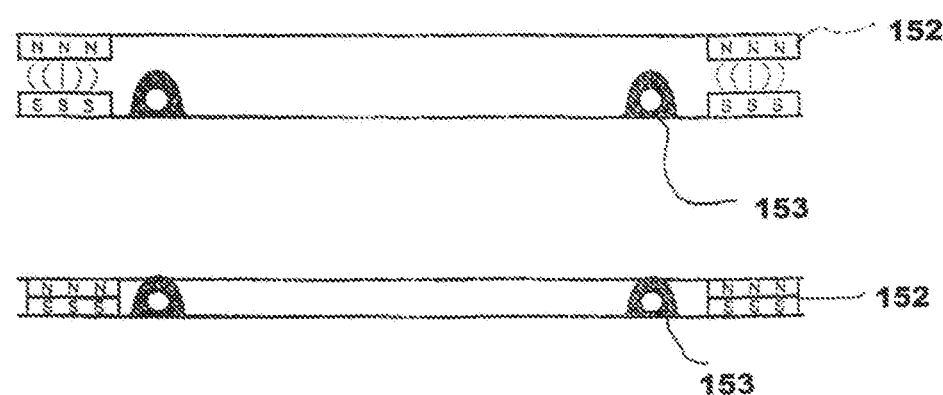
FIG. 15*b* is side view taken along line A-A from FIG. 15*a*.

FIG. 15 shows a wound care device 140 for the treatment of wounds by means of atmospheric negative pressure in the wound region, comprising a wound-covering element that can be attached to the skin of a patient and a connection device (not shown) for the suctioning of fluid media.

The wound-covering element features a window that can be opened 151, which can be attached to the wound-covering element by means of a magnetic seal 152. Furthermore, a surrounding rubber tube 153 is provided in the middle, which is compressed by the tongue and groove seal, producing a gas-tight closure. As an alternative to the rubber tube, a rubber seal, a cork strip or something similar can be provided.

Figure 16A:
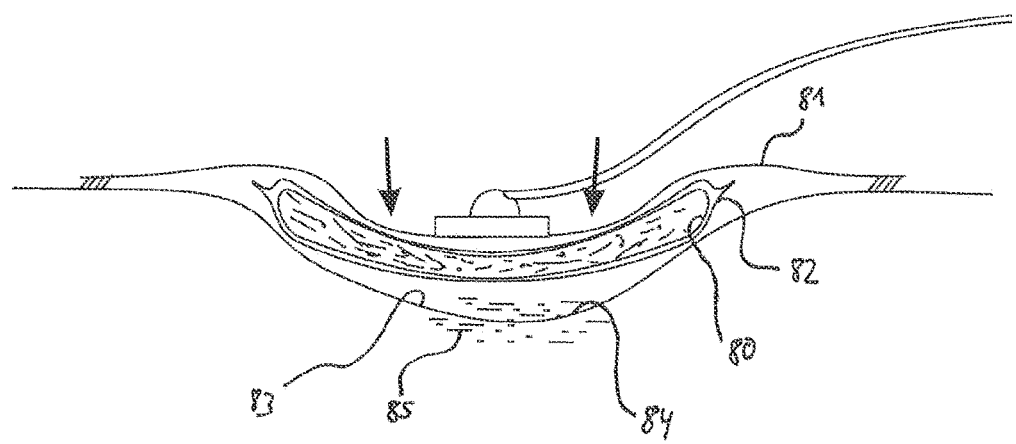
FIG. 16*a* is a side view showing the arrangement of the wound care device according one embodiment with an absorption element 80 with an elastic foil-like element 81 and/or an elastic cover 82 an a deep wound 83 having exudate 85 in its wound base 84.

FIG. 16a shows the arrangement of the invented wound care device with an absorption element 80 with an elastic foil-like element 81 and/or an elastic cover 82 an a deep wound 83 having exudate 85 in its wound base 84. Other than in FIG. 8, the cover 82 may be an integral component of the foil-like element, at least in part—for example in the area facing away from the wound. The elastic foil-like element 81 and/or the elastic cover 82 ensure that when negative pressure is applied, the absorption element can be drawn to or pressed against the wound base 84 (as indicated by the arrows), which is necessary especially with deep wounds in order to establish contact with the exudate 85 that is to be absorbed.

Figure 16B:
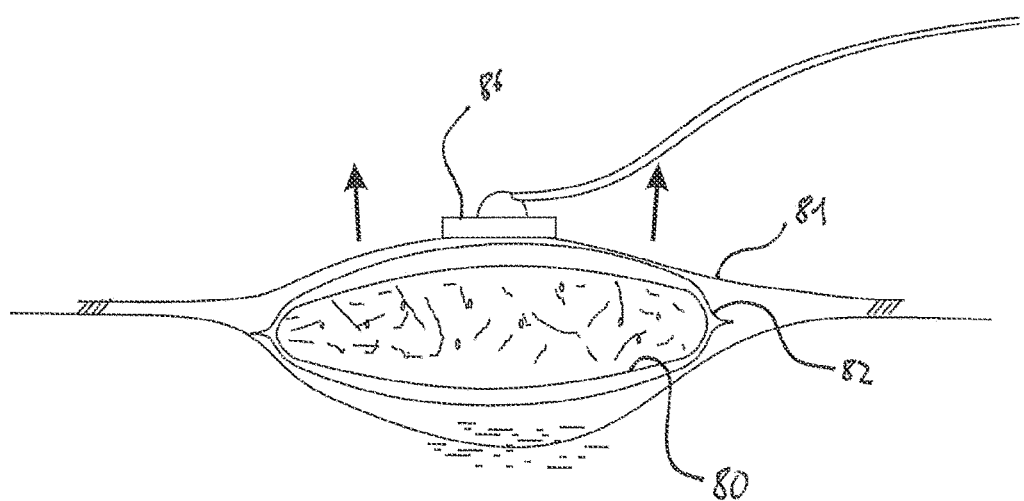
FIG. 16*b* is a side view showing an arrangement similar to the one in FIG. 16*a*, but at a later moment in time, where the absorption element 80 has already absorbed large quantities of exudate.

FIG. 16b shows an arrangement similar to the one in FIG. 16a, but at a later moment in time. The absorption element 80 has already absorbed large quantities of exudate. The elastic foil-like element 81 and/or the elastic cover 82 ensures, the latter are not opposed as a result of the expansion of the absorption element caused by the fluid absorption. This ensures that the absorption element can develop its full absorption capacity. At this time, the coupling facility 86 (and therefore the connected negative pressure device (not shown)) may already be disconnected, or alternatively, the negative pressure device is switched off and no longer applies a negative pressure.

Figure 17:
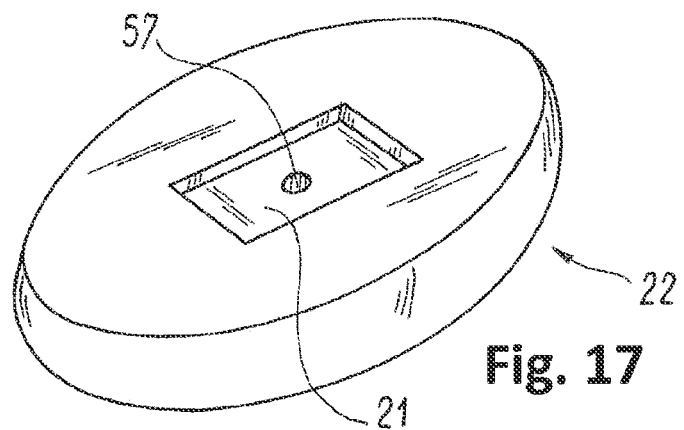
FIG. 17 is a perspective view of an embodiment including a foam material body is devised, featuring a recess especially designed as a compartment for a negative pressure source, for example a pump.

It can also be provided that the application of negative pressures only serves the purpose of drawing the absorption element to the wound base 84 or pressing it against it in order to establish contact with the exudate that is to be absorbed. As soon as this contact is established, it can be provided that the vacuum device is detached or switched off. In this A further embodiment can be seen in FIG. 17. In this embodiment, a foam material body is devised, featuring a recess especially designed as a compartment for a negative pressure source, for example a pump. Preferentially, a check valve (not shown) is placed in a continuous opening 57. The aforementioned foam material body covered by the wound-covering element (not shown).

Figure 18:
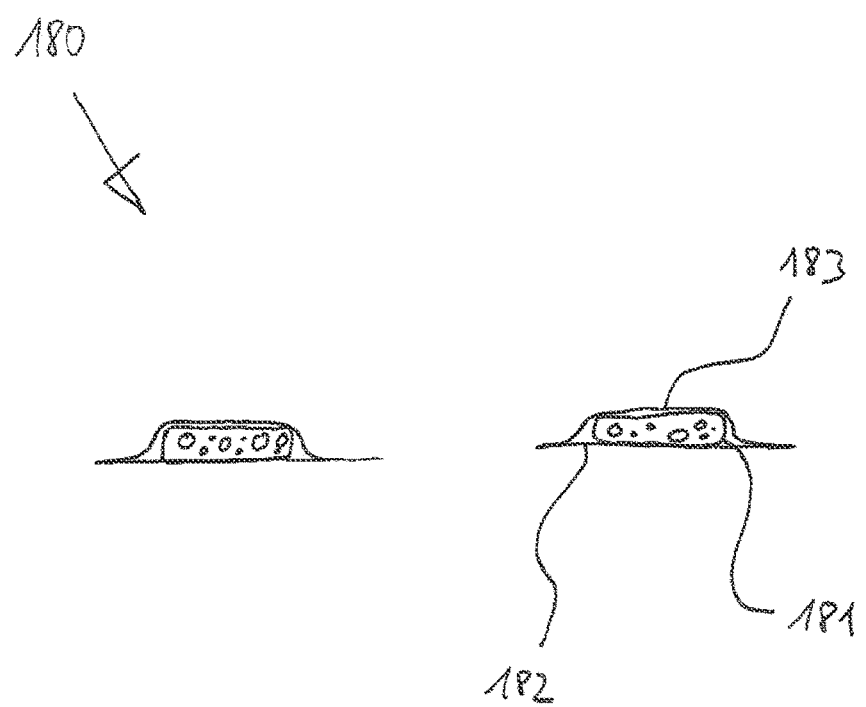
FIG. 18 is a side cross-sectional view showing a frame 180 of a wound-covering element according to one embodiment.

FIG. 18 shows a cross-section through a frame 180 of a wound-covering element according to the invention. The frame may consist, for example, of a foam material 181 which is laminated in a gas-tight base foil 182 and a gas-tight cover foil 183 laminated onto it. The former is the contact surface to the patient's skin, and may, for example, be coated with an adhesive, as coated elsewhere herein. The latter forms the supporting surface for the window that can be opened. Preferentially, it may be embodied in a disinfectable manner.

FIGS. 19 through 22 show concrete embodiments of the invented wound care device.

Figure 19:
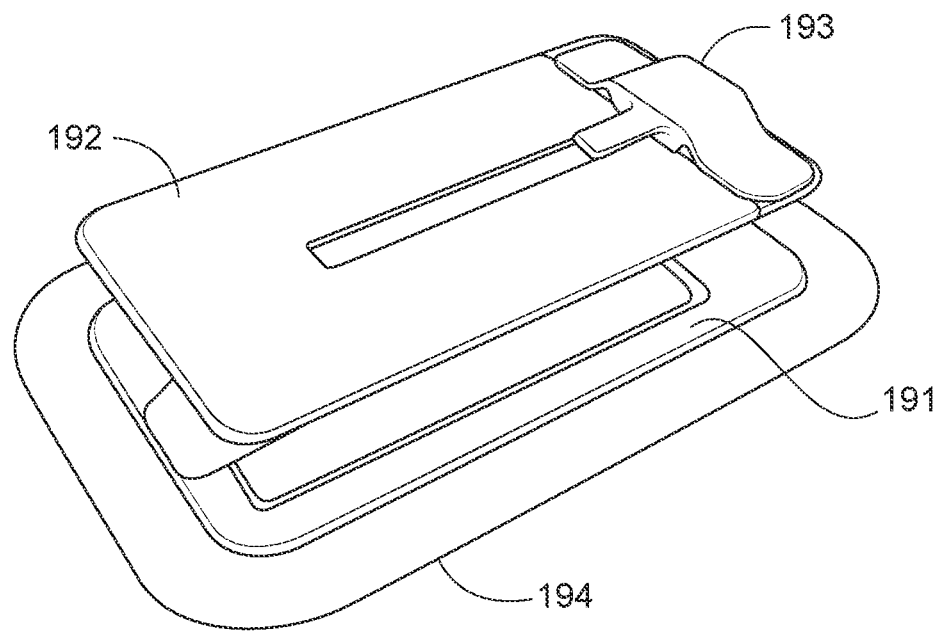
FIG. 19 is a perspective view of a wound care device according to one embodiment for the treatment of wounds by means of atmospheric negative pressure in the wound region, comprising a wound-covering element 191 in the form of a frame that can be attached to the skin of a patient via an underlying foil 194, for example by means of a physiologically safe adhesive, in which the wound-covering element features a window that can be opened 192 that is positioned on the wound-covering element by means of a gas-tight closure.

FIG. 19 shows a wound care device for the treatment of wounds by means of atmospheric negative pressure in the wound region, comprising a wound-covering element 191 in the form of a frame that can be attached to the skin of a patient via an underlying foil 194, for example by means of a physiologically safe adhesive, in which the wound-covering element features a window that can be opened 192 that is positioned on the wound-covering element by means of a gas-tight closure—for example a low-adhesive silicone coating. The wound-covering element [features], for example, a foam material or a spacer fabric laminated in a gas-tight material. The window features a base layer that may feature a foam material or a spacer fabric, for example, which is sealed by a gas-tight foil or coating. In addition, a pump 193 is shown, which is connected to the wound care device via a connection device for the suctioning of fluid media. The window that can be opened 192 features a recess in its material, which forms a compartment for the pump 193.

Figure 20:
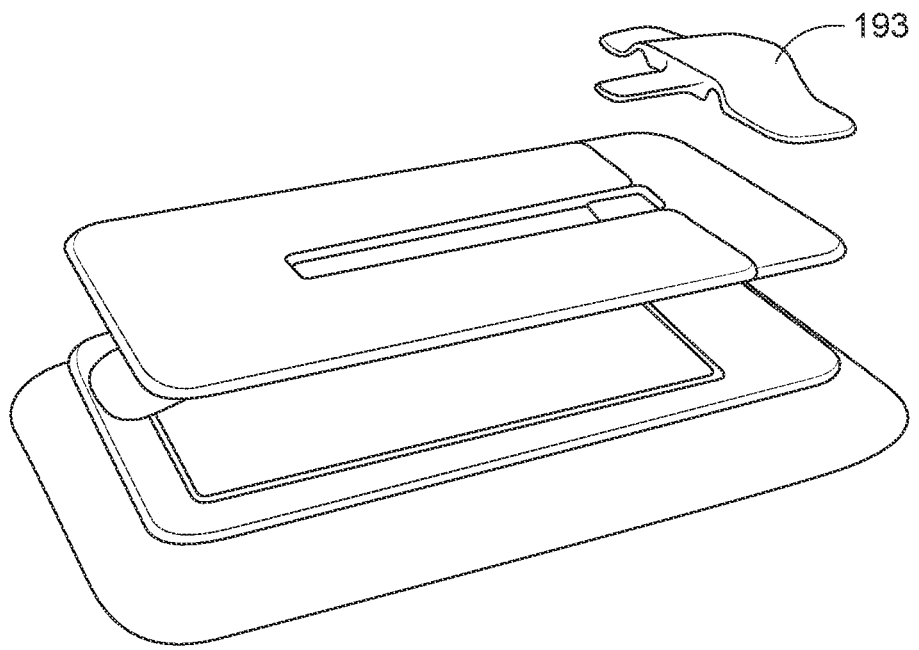
FIG. 20 is a perspective exploded view of a wound care device according to one embodiment, with the wound-covering element 211 in the form of a frame which can be attached to the skin of a patient via an underlying foil 214, for example by means of a physiologically safe adhesive.

The pump 193 is embodied so as to be detachable, as can be seen in FIG. 20.

Figure 21:
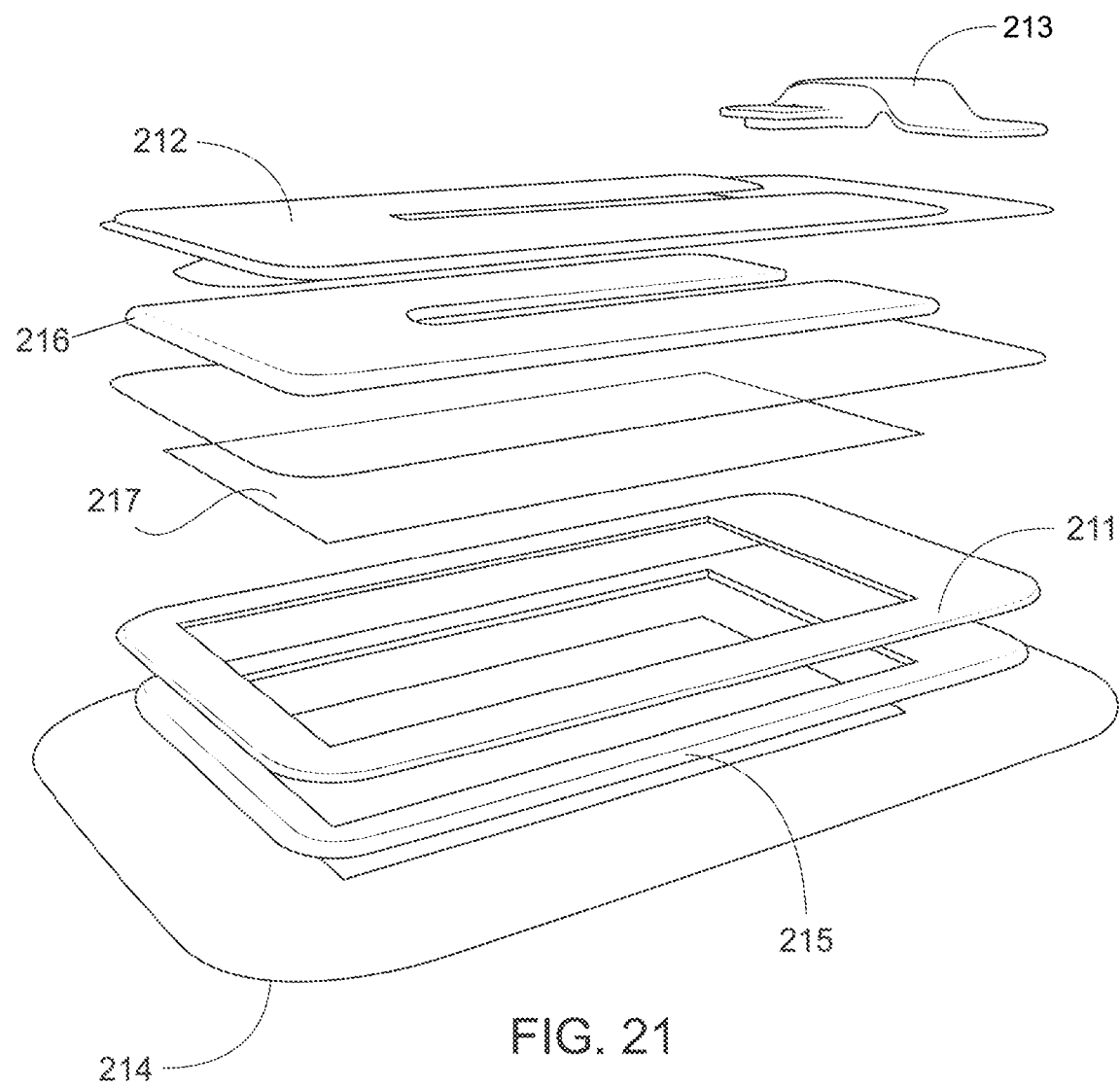
FIG. 21 is a perspective exploded view showing features the window that can be opened 212, which is positioned on the wound-covering element by means of a gas-tight closure, as well as a foam material or spacer fabric 216 underlying the window that is sealed by a gas-tight foil or coating.

FIG. 21 shows the wound care device in exploded view, with the wound-covering element 211 in the form of a frame which can be attached to the skin of a patient via an underlying foil 214, for example by means of a physiologically safe adhesive. Also shown is the foam material or spacer fabric 215 of the wound-covering element 211.

FIG. 21 also shows features the window that can be opened 212, which is positioned on the wound-covering element by means of a gas-tight closure—for example a low-adhesive silicone coating, as well as a foam material or spacer fabric 216 underlying the window that is sealed by a gas-tight foil or coating.

In addition, the pump 213 connected to the wound care device via a connection device for the suctioning of fluid media can be seen, as well as the recess in the window, which forms a compartment for the pump.

In addition, a wound contact lattice 217 is shown which may be positioned either (i) on the wound-facing side, and may be positioned loosely inside the frame or connected to the frame, or (ii) on the cover side.

Figure 22:
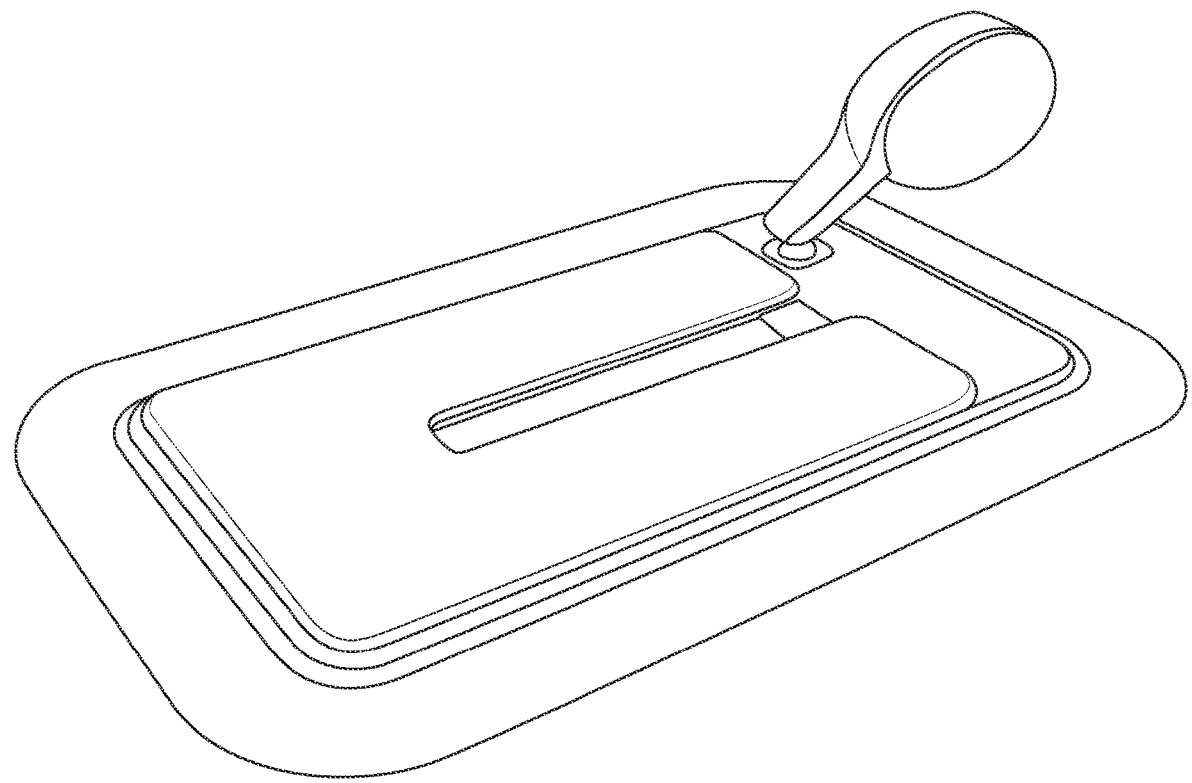
FIG. 22 is a perspective view showing a further wound care device according to one embodiment for the treatment of wounds by means of atmospheric negative pressure in the wound region, in which the pump is embodied as a manually operated pump.

FIG. 22 shows a further wound care device for the treatment of wounds by means of atmospheric negative pressure in the wound region, in which the pump is embodied as a manually operated pump.

All references cited herein are incorporated by reference in their entireties.

While the invention has been described in connection with various embodiments, it will be understood that the invention is capable of further modifications. This application is intended to cover any variations, uses or adaptations of the invention following, in general, the principles of the invention, and including such departures from the present disclosure as, within the known and customary practice within the art to which the invention pertains.

What is claimed is:

1. A wound care device for the treatment of a wound of a patient by means of atmospheric negative pressure, the wound care device comprising:
   a wound covering element configured to be removably attachable to the patient's skin surrounding the wound,
   a window provided in the wound covering element that is configured to open be openable to permit access to the wound and closeable on the wound covering element to form a gas-tight closure,
   a vacuum connection coupled to the window, and
   a wound exudate-extracting absorption element disposed adjacent to a wound-facing side of the window, the wound exudate-extracting absorption element comprising at least one super-absorbing substance surrounded by a cover that is permeable to fluids,
   wherein the wound covering element is capable of moving in conjunction with movements of the patient's skin to whom the wound covering element is removably attached while retaining gas-tightness of the gas-tight closure, and
   wherein the wound covering element includes a pleated arrangement or comprises one or several stretch bellows such that, when the wound covering element is removably attached to patient's skin, the window is closable on the wound covering element to form the gas-tight closure by interlocking the window and the wound covering element together.

2. The wound care device according to claim 1, wherein the wound covering element has a preformed geometry adapted to conform to an anatomic form of the skin to which the wound covering device is capable of being removably attached.

3. The wound care device according to claim 1, wherein the wound covering element further comprises an adhesive material selected from the group consisting of acrylic, silicone, hydrocolloid, zinc oxide and latex.

4. The wound care device according to claim 1, further comprising a wound contact lattice permeable to fluids.

5. The wound care device according to claim 1, further comprising a barrier that is at least semipermeable to liquids, the barrier being positioned in the wound care device such that it restricts fluid passage into a vacuum flow through the vacuum connection.

6. The wound care device according to claim 1, further comprising a vacuum source capable of generating an atmospheric negative pressure.

7. The wound care device according to claim 6, wherein the vacuum source further comprises a pump coupled to the vacuum connection.

8. The wound care device according to claim 7, wherein the pump is coupled to the wound covering element.

9. The wound care device according to claim 6, further comprising one of a coupling, a blocking valve and a three-way valve positioned between the vacuum source and one of the wound covering element and the wound exudate-extracting absorption element.

10. The wound care device according to claim 1, further comprising a spacer between the wound covering element and a wound to which the wound covering element is applied.

11. The wound care device according to claim 1, further comprising an antibacterial material layer.

12. The wound care device according to claim 11, wherein the antibacterial material layer further comprises at least one of a heavy metal, copper, silver and salts thereof.

13. The wound care device according to claim 1, wherein the wound covering element is fluid impermeable.

14. The wound care device according to claim 7, wherein the pump is reversible such that the atmospheric negative pressure is capable of being reversed.

15. The use of the wound care device of claim 1 in treating a wound selected from the group consisting of soft tissue defects, infected wounds post-surgical debridement, lymphatic fistulae, sternal wound infections, thoracic wall ports, pressure sores, venous ulcers, chronic wound healing disorders, radiation ulcers, abdominal compartment syndrome, septic abdomen, enteral fistulae, and/or wounds caused by one or several edemas, for fixing skin transplants, for wound conditioning, and/or for postoperative care of sutures and incisions.

16. The use of the wound care device of claim 1 in a wound compression system.

17. The wound care device of claim 1, wherein the wound exudate-extracting absorption element further comprises first and second layers of superabsorbing polymer.

18. The wound care device of claim 17, further comprising an elastic cover enclosing the exudate-extracting absorption element.

19. The wound care device of claim 18, further comprising an elastic element disposed over the exudate-extracting absorption element.

20. The wound care device according to claim 1, wherein the window is openable and closeable when the wound covering element is removably attached to patient's skin without exerting a pressing down force on the wound.

21. The wound care device according to claim 1, wherein the window is openable and closeable when the wound covering element is removably attached to patient's skin without exposing the patient to pain.

\* \* \* \* \*

UNITED STATES PATENT AND TRADEMARK OFFICE
CERTIFICATE OF CORRECTION

PATENT NO. : 11,154,426 B2  
APPLICATION NO. : 14/942038  
DATED : October 26, 2021  
INVENTOR(S) : Birgit Riesinger It is certified that error appears in the above-identified patent and that said Letters Patent is hereby corrected as shown below:

In the Claims

In Column 19, Line 61, delete "open" between "to" and "be openable"

Signed and Sealed this  
Fifteenth Day of February, 2022

Drew Hirshfeld  
*Performing the Functions and Duties of the*  
*Under Secretary of Commerce for Intellectual Property and*  
*Director of the United States Patent and Trademark Office*